US005640960A

United States Patent [19]
Jones et al.

[11] Patent Number: 5,640,960
[45] Date of Patent: Jun. 24, 1997

[54] HAND-HELD, BATTERY OPERATED, DOPPLER ULTRASOUND MEDICAL DIAGNOSTIC DEVICE WITH CORDLESS PROBE

[75] Inventors: David C. Jones, Evergreen; Dennis R. Newman, Golden, both of Colo.

[73] Assignee: Imex Medical Systems, Inc., Golden, Colo.

[21] Appl. No.: 425,044

[22] Filed: Apr. 18, 1995

[51] Int. Cl.$^6$ .................................................. A61B 8/06
[52] U.S. Cl. .................... 128/661.07; 128/661.08
[58] Field of Search .................... 128/660.01, 662.03, 128/662.04, 661.07–661.1, 630, 672, 691, 732, 653.1

[56] References Cited

U.S. PATENT DOCUMENTS

| | | | |
|---|---|---|---|
| 3,753,433 | 8/1973 | Bakerich et al. | 128/732 |
| 4,276,491 | 6/1981 | Daniel | 128/662.04 |
| 4,413,629 | 11/1983 | Durley, III | 128/662.04 |
| 4,677,982 | 7/1987 | Llinas et al. | 128/664 |
| 4,681,111 | 7/1987 | Silvian | 128/697 X |
| 4,694,837 | 9/1987 | Blakeley et al. | 128/696 X |
| 4,807,636 | 2/1989 | Skidmore et al. | 128/661.1 |
| 4,850,364 | 7/1989 | Leavitt | 128/661.09 |
| 4,958,645 | 9/1990 | Cadell et al. | 128/671 |
| 5,038,785 | 8/1991 | Blakeley et al. | 128/671 X |
| 5,177,691 | 1/1993 | Welles et al. | 364/485 |
| 5,183,040 | 2/1993 | Nappholz et al. | 128/661.07 X |
| 5,394,878 | 3/1995 | Frazin et al. | 128/662.06 |

OTHER PUBLICATIONS

IMEXDOPCT+ Product Brochure, DEAL 30K0193 M7–0260–AO, Issued by IMEX Medical Systems Inc., Golden Colorado, U.S.A. (1993).

"Optoelectronics DataBook 1993" Issued by Siemens Corporation, Inc. Optoelectronics Division of Cupertino, California, U.S.A. (1993).

"RF Communications Handbook" Issued by Signetics Company, a division of North American Philips Corporation (1990).

"Communication Techniques for Digital and Analog Signals," Morton Kanefsdy, Harper & Row Publishers, Inc. (1985).

"Sound Transmission with Free Propagating Infrared Light, Part 2: Discontinuous Modulation Techniques," H.J. Griese, Audio Engineering Soc., 91982).

"Solid State Radio Engineering," Herbert L. Krauss, Charles W. Bostian, and Frederick H. Raab, John Wiley & Sons, Inc. (1980).

*Primary Examiner*—Francis Jaworski
*Attorney, Agent, or Firm*—James R. Young; Scott B. Allison; Chrisman, Bynum & Johnson, P.C.

[57] ABSTRACT

A hand-held, battery operated, Doppler ultrasound diagnostic device for use in obstetrical applications to, for example, measure fetal heartbeat, and vascular applications to, for example, measure blood flow and pressure, includes a cordless probe, a base unit, and an electric recharging stand. The probe detects the physical response signal being monitored through Doppler ultrasound techniques. The signal is used to frequency modulate a sine wave carrier signal which is transmitted by the probe and received by the base unit. The carrier signal frequency and wave form is chosen so as not to cause interference with other medical equipment that may be nearby. The base unit demodulates the carrier signal and retrieves the human response signal. The base unit displays the human response signal visually with an LED display and audibly with built in speakers. In addition, the base unit includes an output connectors which allow the human response signal to be recorded on a tape recorder or played through earphones. Having a cordless probe enables the base unit to be placed outside the sterile field created around the patient. When not in use, the probe can be stored in a nested position in the base unit and the base unit can be attached to the recharging stand. Both the probe and the base unit are battery operated. The base unit will recharge its batteries when positioned in the recharging stand. The probe will recharge its batteries when the probe is positioned in the base unit and the base unit is positioned in the recharging stand.

15 Claims, 13 Drawing Sheets

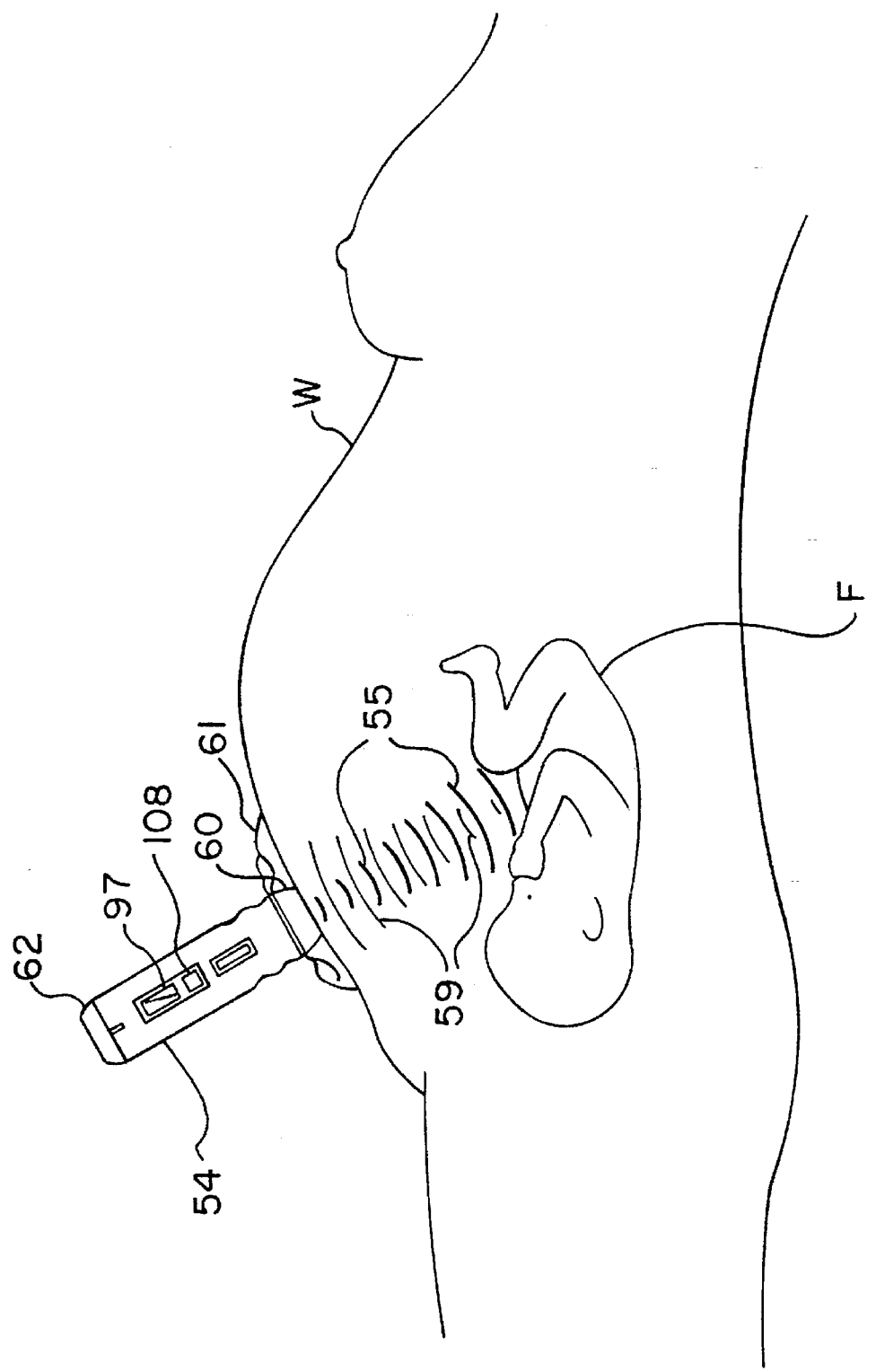

HAND-HELD, BATTERY OPERATED, DOPPLER ULTRASOUND MEDICAL DIAGNOSTIC DEVICE WITH CORDLESS PROBE

BACKGROUND OF THE INVENTION

1. Field of the Invention

The present invention is directed generally to a medical diagnostic devices that use Doppler ultrasound for obstetrical and vascular monitoring applications, and more specifically to a system for wireless transmission of signals derived from a Doppler ultrasound probe to a base unit for visual display, audible display, and recordation.

2. Description of the Prior Art

The diagnostic capabilities of the medical profession have increased significantly throughout the years. Two such advancements have been in the use of Doppler ultrasound based devices to detect and measure vascular and cardial blood flow direction and rate, to detect and measure fetal heart rate, and for numerous other diagnostic applications.

The basic Doppler effect for sound is well-known. When a source of sound and a receiver of the sound move in relation to each other, the pitch or frequency of the sound perceived or detected at the receiver is different from the pitch or frequency of the source. If they are moving toward each other, the perceived or received pitch or frequency of the sound is higher than the source sound. The classic example is standing near a railroad track as a train blowing its whistle passes. As the train approaches, the perceived whistle sound is a high pitch, which then changes abruptly to a lower pitch as the train passes and goes away from the listener.

Ultrasound is simply sound that has a higher pitch or frequency than the hearing capability of a normal human ear, which is about 20 kilohertz (KHz). The Doppler effect for ultrasound is the same as for audible sound, but, since ultrasound is at a pitch or frequency beyond the range of human ears, electronic equipment is used to detect it.

The Doppler effect is also produced in echoes, when sound or ultrasound is reflected by, or bounced off, a moving object. Thus, sound or ultrasound can be produced and projected by a speaker device or ultrasound sender, and, if it reflects or bounces off an object or target, the echo or return sound can be received and detected. If the ultrasound source, target object, and echo receiver are all stationary, the pitch or frequency of the echo ultrasound will be the same as the source ultrasound. However, if the target object is moving toward the receiver of the ultrasound echo, the ultrasound echo received and detected will have a higher pitch than if the target object was moving away from the receiver. The speed or velocity at which the target object is moving toward or away from the receiver determines the pitch or frequency of the echo received. Also, a fluid, such as blood, also reflects ultrasound waves, and the velocity or rate of blood flow determines the frequency of the echoed ultrasound waves. Thus, detecting frequencies of the echoed ultrasound waves can be used to measure direction and rate of blood flow. This Doppler effect in echoed ultrasound is the principle that is typically utilized in ultrasound medical diagnostic devices, where ultrasound signals having frequencies in the range between one (1) megahertz (MHz) and twenty (20) MHz are often used.

In medical diagnostic devices using Doppler ultrasound, the source of the ultrasound and the receiver of the ultrasound are usually transducers mounted in a hand-held probe. The probe is held relatively stationary with respect to a target object being detected or measured. Some slow movement and positioning of the probe by the physician or technician can be accommodated for detecting, if it is substantially slower than the motion of the target object. However, where accurate measurements are needed, the probe should be held quite stationary. An ultrasound wave stream is transmitted by the transducer in the probe in the direction of the target object to be detected or measured, and the return echo is received, transduced to an electric signal having both a frequency and an amplitude that corresponds to the frequency and amplitude of the echoed ultrasound waves. For example, in obstetrical applications, such as detecting or measuring fetal heart rate, the ultrasound waves from the probe are directed so as to intercept the blood flowing in a beating fetal heart. In vascular applications, the ultrasound waves from the probe are directed to intercept blood moving and circulating in a vein or artery to detect or measure blood flow and direction. In both situations, the directed signal from the probe is reflected by the flowing blood, which creates Doppler shifts from the frequency of the ultrasound by the probe to the frequencies of the echoed ultrasound reflected from the flowing blood. The reflected ultrasound echoes from the flowing blood is detected by a transducer in the probe, which converts ultrasound wave energy to electric signals. The Doppler frequency shift between the directed ultrasound and the reflected ultrasound echoes returned from the flowing blood varies proportionally with the instantaneous velocity of the flowing blood. If the blood is flowing away from the directed ultrasound from the probe, the reflected ultrasound echoes will have lower frequencies than the directed ultrasound. If the blood is flowing toward the directed ultrasound from the probe, the reflected ultrasound echoes will have higher frequencies than the directed ultrasound. Of course, if the moving target is not moving in relation to the directed ultrasound from the probe, the reflected ultrasound echo will have the same frequency as the directed ultrasound.

Doppler ultrasound techniques for medical diagnostic purposes are well known in the art. For example, see Peter Atkinson & John Woodcock, DOPPLER ULTRASOUND AND ITS USE IN CLINICAL MEASUREMENT, published by Academic Press of New York City (1982); Matthew Hussey, BASIC PHYSICS AND TECHNOLOGY OF MEDICAL DIAGNOSTIC ULTRASOUND, published by Elsevier of New York City (1985); and Peter Fish, PHYSICS AND INSTRUMENTATION OF DIAGNOSTIC MEDICAL ULTRASOUND, published by John Wiley & Sons of New York City (1990). See also, U.S. Pat. Nos. 4,276,491 issued to Daniel; 4,807,636 issued to Skidmore et al.; 4,850,364 issued to Leavitt; and 5,394,878 issued to Frazin all of which show medical devices using Doppler ultrasound techniques. Furthermore, Doppler ultrasound has become a popular method of medical diagnosis because it is non-invasive, painless, creates little or no side effects, and is relatively inexpensive. Finally, ultrasound frequencies are often used in medical diagnostic applications because they reflect well from the boundaries between different organs and blood cells without utilizing potentially harmful ionizing radiation.

In many medical diagnostic applications using Doppler ultrasound, the transmitter of the directed signal is placed directly against the human skin. For example, when measuring fetal heart rate, the transmitter is placed on the midline of the abdomen and aimed downward toward the pubic bone. When measuring vascular flow, the transmitter is placed directly over the underlying vessel. The direct contact between the transmitter and the human skin is necessary to reduce reflections of the directed ultrasound and the reflected ultrasound echo caused by the skin, and ultrasound does not propagate well in air at the frequencies used in these applications. To facilitate ease of use and manual manipulation of diagnostic devices using Doppler ultrasound, as described above, it is desirable to have a device that is small, portable, and battery operated, since the probe must often be placed directly next to the skin of the patient being tested. Current Doppler ultrasound probes are connected by a cord containing electric wires to a base unit, where the electric signals from the receiving transducer are processed for display in useful information format. While such current devices are very useful and effective, there has been a need for even further improvements-one of which is to eliminate the cord between the probe and the base unit. A cordless probe would make the probe easier to handle and use, and it would reduce the amount of equipment placed in the sterile field around the patient. A cordless probe would also enable the person using the diagnostic device to place the probe in any desired position, unencumbered by a cord and the positioning restrictions that a cord might impose. There are some constraints, however, in replacing the cord with some kind of wireless signal transmission system between the probe and the base unit. For example, the signal transmitted from the probe to the base unit cannot interfere with other medical equipment in the room, hospital, or ambulance. The signal transmitted from the probe to the base unit may also interfere with the operation of the Doppler transceiver, itself, if the harmonics coincide with the Doppler signal. Furthermore, since Doppler ultrasound in an obstetrical application is often used to reassure the mother of the presence of fetal life, it is crucial that the signal from the probe be received by the base unit in a very reliable manner, regardless of its position in relation to the base receiver and to other objects and persons in the room, to avoid alarming the mother. Finally, it is desirable to have the batteries used in the probe and the base unit be rechargeable during storage of the base unit and the probe so that the batteries will be fully charged when the probe and the base unit are used.

SUMMARY OF THE INVENTION

Accordingly, it is a general object of this invention to provide a hand-held, battery operated, and cordless ultrasound transceiver device for use in obstetrical, cardiovascular, and other diagnostic applications.

It is another general object of this invention to provide ultrasound medical diagnostic equipment including a hand-held freely moveable probe containing ultrasound producing and receiving components and a base unit for processing the Doppler frequency shifted information into visual and/or audibly perceivable useful information with wireless transmission of signals from the probe to a base unit.

It is a specific object of this invention to provide a medical diagnostic device including a probe and a base unit, wherein the probe transmits a signal that is received reliably and consistently by the base unit regardless of the orientation, position, and location of the probe in relation to the base unit or in relation to other objects and/or persons in the room.

Another specific object of this invention to provide ultrasound medical diagnostic equipment including a hand-held freely moveable probe containing ultrasound producing and detecting components and a base unit wherein signals transmitted by the probe and received by the base unit do not interfere with other nearby medical or communications equipment or with the ultrasound operations of the probe itself.

Additional objects, advantages, and novel features of the invention shall be set forth in part in the description that follows, and in part will become apparent to those skilled in the art upon examination of the following or may be learned by the practice of the invention. The objects and the advantages may be realized and attained by means of the instrumentalities and in combinations particularly pointed out in the appended claims.

To achieve the foregoing and other objects and in accordance with the purposes of the present invention, as embodied and broadly described therein, the present invention includes a transducer, sensitive to physical phenomena in a body, that produces a first electric signal having characteristics indicative of the physical phenomena; a signal converter for converting the first electric signal into a frequency modulated sine wave current signal that drives a light emitter where the light emitted has an intensity that is a linear function of the amplitude of the frequency modulated sine wave current signal; a light detector spatially separate from the light emitter for detecting the emitted light signal and producing a corresponding second electric signal; a signal processor for extracting the first electric signal from the second electric signal, and a audible display, visual display, and a recorder connection for displaying and recording the information indicative of the physical phenomena.

To further achieve the foregoing and other objects, the present invention further comprises a method of measuring fetal heart rate or vascular or cardial blood flow using Doppler ultrasound techniques, by generating a first electric signal having a frequency in the ultrasound range; generating directed ultrasound waveforms having the same frequency as the electric signal; directing the ultrasound waveforms toward flowing blood or a beating heart; detecting reflected ultrasound waveforms reflected by the flowing blood or the beating heart; producing a second electric signal having the same frequency as the reflected ultrasound waveforms; heterodyning the first electric signal and the second electric signal to create a mixed electric signal having a frequency that is proportional to the velocity of the flowing blood or the beating heart; frequency modulating a carrier signal with the mixed electric signal to produce a frequency modulated sine wave electric signal; driving a light emitter with the frequency modulated sine wave electric signal to produce a frequency modulated sine wave light signal; detecting the frequency modulated sine wave light signal with a detector to produce a third electric signal; and frequency demodulating the third electric signal to recover the mixed electric signal.

BRIEF DESCRIPTION OF THE DRAWINGS

The accompanying drawings, which are incorporated in and form a part of the specifications, illustrate the preferred embodiments of the present invention, and together with the descriptions serve to explain the principles of the invention. In the Drawings:

FIG. 2 shows an isometric view of the ultrasound probe of the medical diagnostic device of FIG. 1 shown with a nose mounted on one end for emitting and detecting ultrasound waves and illustrating ultrasound waves propagating toward a fetal heart and reflected echo ultrasound waves returning to the probe;

DETAILED DESCRIPTION OF THE PREFERRED EMBODIMENTS

Figure 1:
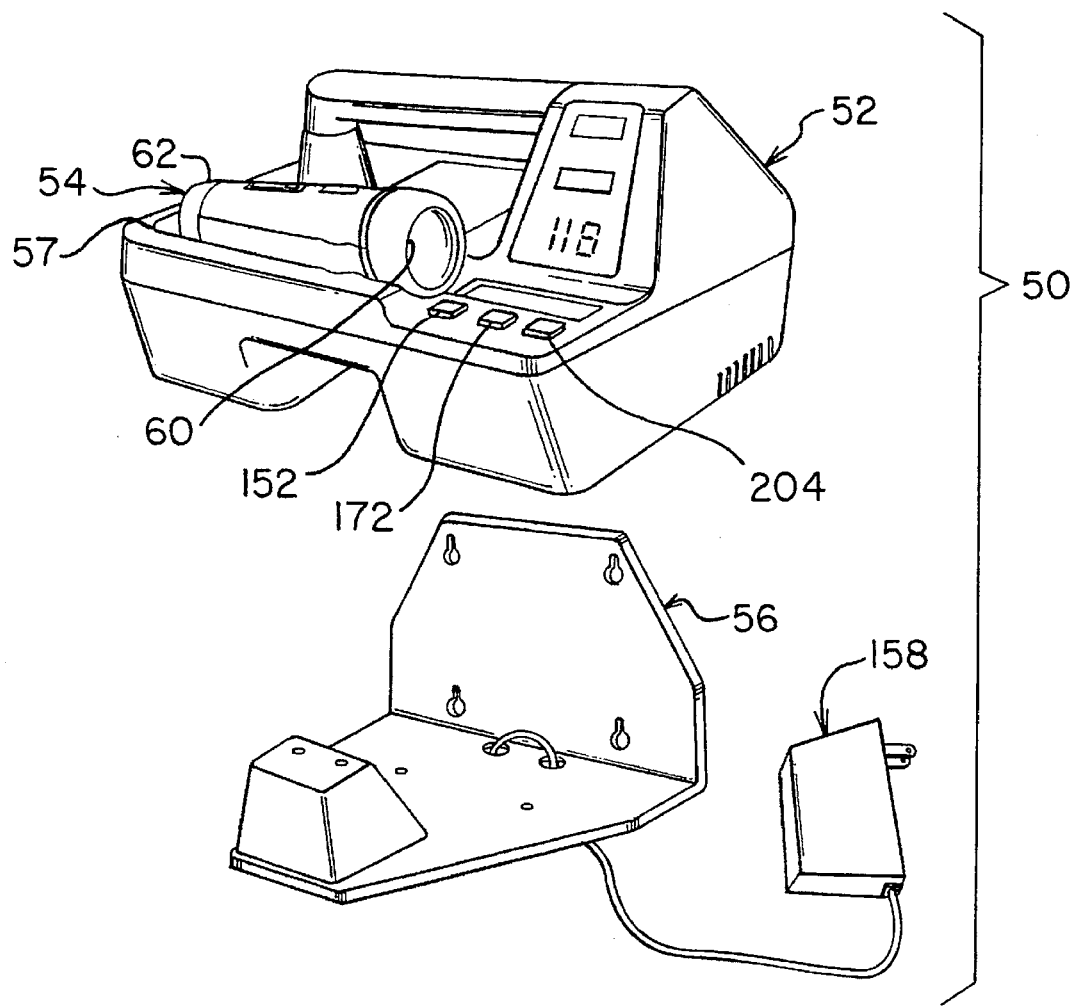
FIG. 1 is an isometric view of the ultrasound medical diagnostic device of the present invention, including a base unit, a probe, and a recharging stand.

The ultrasound medical diagnostic device 50 of the present invention shown in FIG. 1 includes a base unit 52 for receiving light signals emitted by a probe 54, the probe 54 for emitting and receiving ultrasound waves and for emitting light signals, and a recharging stand 56 for storing and recharging the base unit 52 and the probe 54. The probe 54 can be positioned in probe holder 57 in the base unit 52 for storage when the medical diagnostic device 50 is not being used. Likewise the base unit 52 can be placed into the recharging stand 56 for storage when the medical diagnostic device 50 is not being used, and for recharging the rechargeable battery 107 in the probe 54 and the rechargeable battery 154 in the base unit 52.

Figure 3:
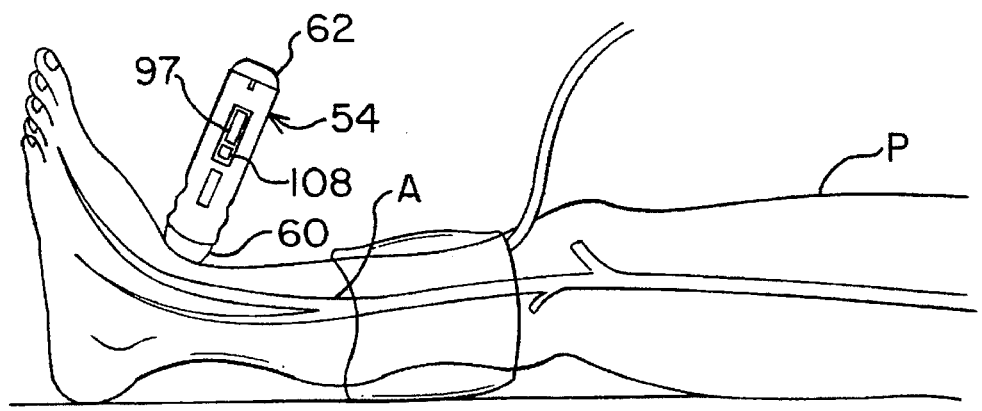
FIG. 3 shows an isometric view of the ultrasound probe of the medical diagnostic device of FIG. 1 shown with a nose mounted on one end for emitting and detecting ultrasound waves and illustrating use of the medical diagnostic device in a vascular application.

During use, the detachable nose 60 end of the probe 54 is placed next to the skin of a patient, as shown in FIGS. 2 and 3. The probe 54 emits ultrasound waves 55 at a constant frequency toward a moving target, for example, blood (not shown) flowing in the heart (not shown) of a fetus F of a pregnant woman W (see FIG. 2), or the blood (not shown) flowing in an artery A, of the patient P being monitored (see FIG. 3).

Referring to FIG. 2, the blood (not shown) flowing in the heart of the fetus F reflects the ultrasound waves 55 transmitted from the probe 54 and causes a Doppler frequency shift in the reflected ultrasound waves 59 that corresponds to the velocity of flowing blood (not shown). An electric signal having a frequency that is in the audible hearing range of a human ear and which is still proportional to the velocity of the flowing blood being targeted and which can be used to drive a speaker in the base unit 52 to produce audible sound that can be heard by the operator and by the patient, can be created by a conventional heterodyne process. Essentially, a constant frequency electric signal is produced to drive or oscillate an ultrasound producing or sending transducer in the probe 54, which produces and propagates the ultrasound waves 55 at that constant frequency. An ultrasound receiving transducer in the probe 54 detects the reflected ultrasound echo waves 59 and produces an electric signal that has the same frequency as, and an amplitude proportional to, the reflected ultrasound waves 59. In the heterodyne process, the electric signal with the sending frequency is mixed with the electric signal of the reflected frequency, which produces an electric signal that has a beat frequency equal to the difference between the respective sending frequency and reflected frequency. The beat frequency varies between zero, when there is no difference between the sending frequency and the reflected frequency, to some frequency in the audible hearing range, when the moving target, for example, flowing blood or a beating heart, and the beat frequency is proportional to the velocity of the moving target. An audio frequency electric signal can be produced from this heterodyne beat frequency for driving a speaker that can be heard by the operator and patient, as described above, as well as for driving calculations and visual displays of heart rate, blood flow velocity, and the like. The audio frequency electric signal is transmitted by infrared light from the probe 54 to the base unit 52 as will be described in more detail below, where it can be processed for visual display, played over speakers, or recorded.

Propagation of the ultrasound waves 55 and the reflected waves 59 can be improved by applying coupling gel 61 (see FIG. 2) to the skin of the patient and the detachable nose 60 of the probe 54. The coupling gel 61 acts as a transfer medium through which the ultrasound waves 55 emitted by the sender element 90 and the reflected waves 59 can travel.

Figure 4:
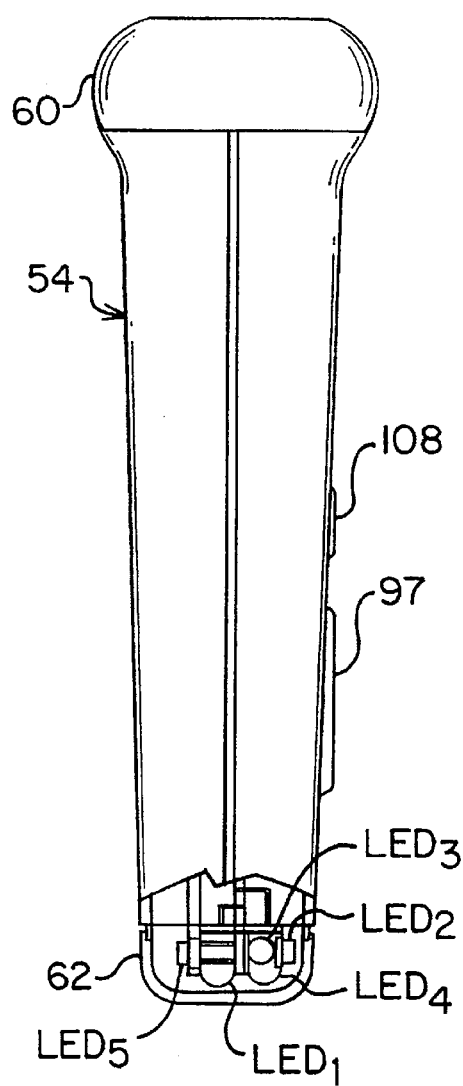
FIG. 4 shows a side view of the ultrasound probe of the medical diagnostic device of FIG. 1.
Figure 10:
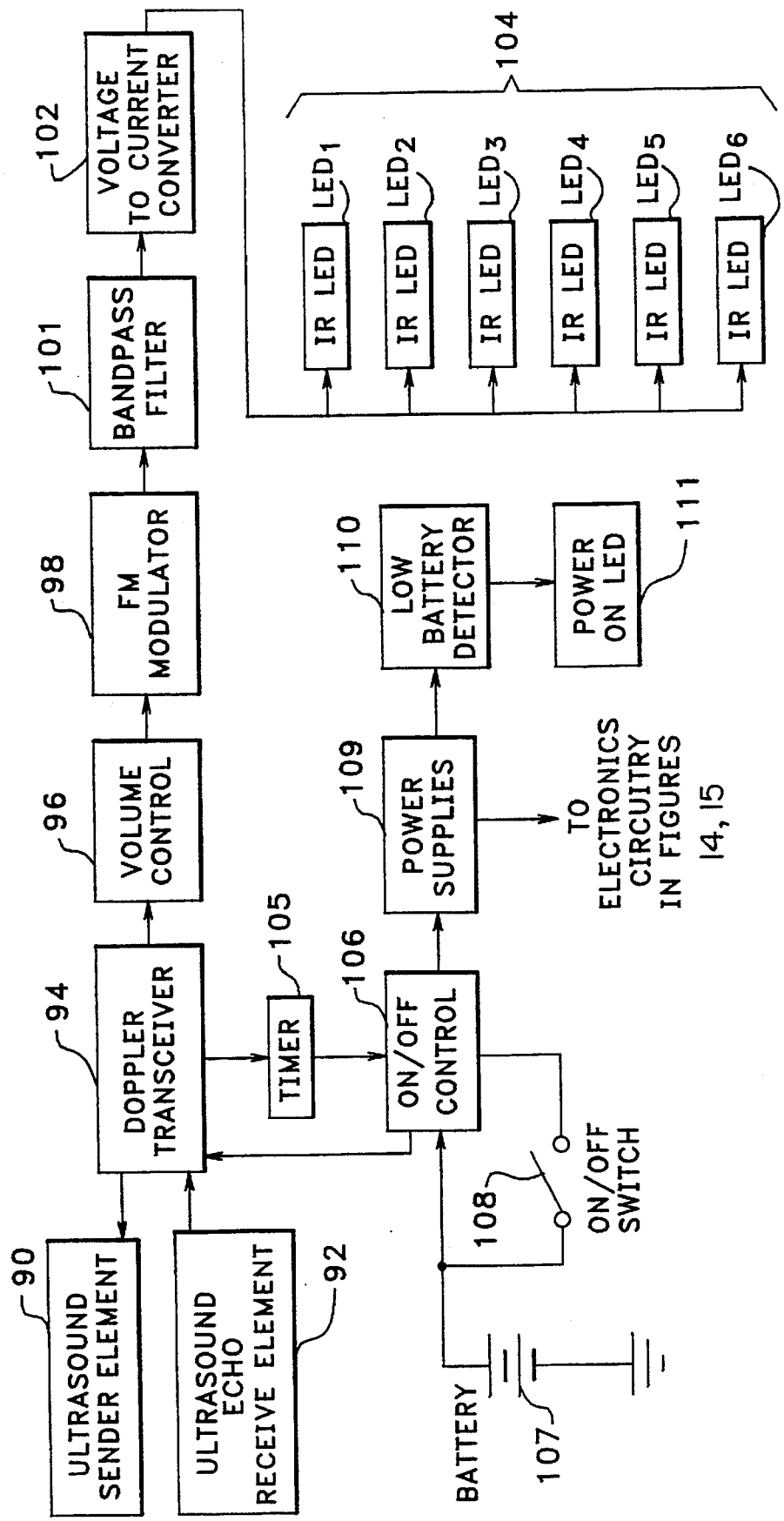
FIG. 10 shows a functional block diagram of the operative components and electronic circuitry of the ultrasound probe of FIG. 1 constructed according to the present invention.
Figure 12:
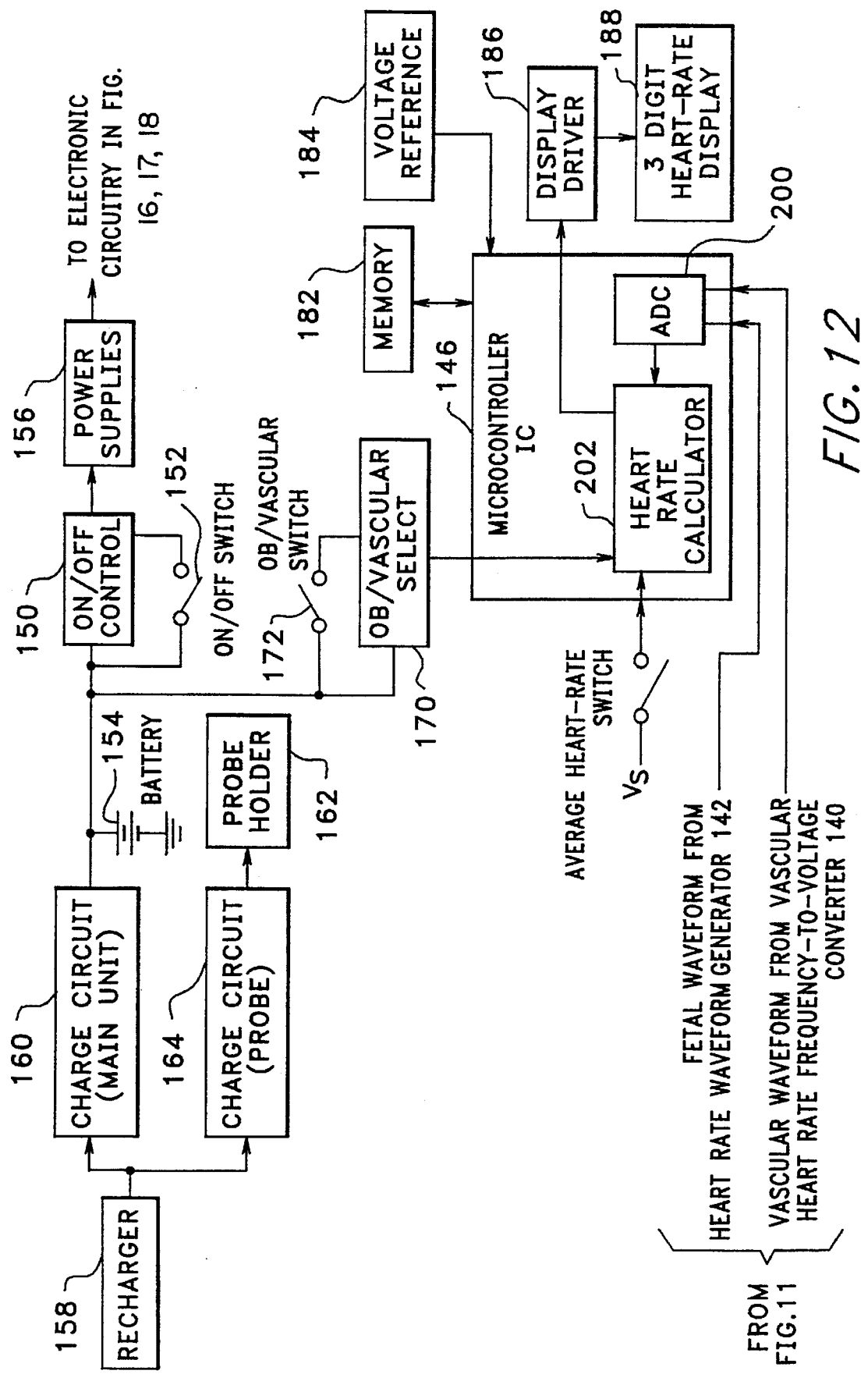
FIG. 12 shows an operational block diagram of the on/off, power supply, and microcontroller portion of the electronic circuitry of the base unit and the recharging stand shown in FIG. 1.

The functional block diagram for the components and electronic circuitry in the probe 54 is shown in FIG. 10, while the functional block diagram for the components and electronic circuitry in the base unit 52 is shown in FIGS. 4 and 5. The functional block diagram for the recharging stand 56 is also shown in FIG. 12.

Referring now to FIG. 10, the components of the probe 54 will now be discussed in greater detail. The power of the probe 54 is controlled by the on/off control 106. The user activates the probe 54 by placing the on/off control 106 in the "on" state by momentarily pressing the on/off switch 108, which momentarily places the on/off switch 108 in the "on" state. The on/off control 106 is changed to the "off" state the next time the on/off switch 108 is momentarily pressed.

The on/off control 106 provides connection between the battery 107 and the power supplies 109 when the on/off control 106 is in the "on" state. The power supplies 109 take the voltage supplied by the rechargeable battery 107 and convert it to create the necessary power, voltages, and voltage levels used by the electronic components in the electronic circuitry in the probe 54. When the on/off control 106 is in the "off" state, the rechargeable battery 107 is disconnected from the electronic circuitry in the probe 54. The use of power supplies and power supply circuity to create different voltage levels is well known to people having ordinary skill in the art and need not be described in any further detail.

The power supplies 109 also provide an output signal to the low battery detector 110, which monitors the charge and energy level of the rechargeable battery 107 to determine if the rechargeable battery 107 is losing its power or charge. When the on/off control 106 is in the "on" state and the rechargeable battery 107 is operating with enough charge to drive the electronic circuitry in the probe 54, the low battery detector 110 provides a signal to the power on LED 111 so as to cause the power on LED 111 to emit a continuous visible light. When the on/off control 106 is in the "on" state and the rechargeable battery 107 is not operating with enough charge, the low battery detector 110 provides a signal to the power on LED 111 so as to cause the power on LED 111 to emit a flashing visible light as an indicator to the user that the rechargeable battery 107 is low on charge. Six V17OR cells manufactured by Varta Batteries, Inc., can be used in the rechargeable battery 107 in this invention. The HLMP-M501 manufactured by Quality Technologies can be used for the "power on" LED 111 in this invention. This type of power level indication circuitry is well known to people having ordinary skill in the art and need not be described in any further detail.

When the on/off control 106 is in the "on" state, the Doppler transceiver 94 is activated. When the on/off control 106 is in the "off" state, the Doppler transceiver 94 is not activated. Doppler transceivers are well known in the art. For example, the FP3B manufactured by Medasonics of Fremont, Calif., can be used in this invention for the Doppler transceiver 94. The Doppler transceiver 94 creates the constant frequency electric signal which drives the ultrasound sender element or transducer 90 located in the detachable nose 60 (see FIGS. 2-5) of the probe 54 to produce and propagate the constant frequency ultrasound waves 55. The Doppler frequency shifted return ultrasound waves 59 are detected by the receive dement or transducer 92, which is also located in the detachable nose 60 of the probe 54 and controlled by the Doppler transceiver 94. The detachable nose 60 provides access to the rechargeable battery 107 for replacement. The sender dement 90, receive element 92, and the Doppler transceiver 94 can be designed for a specific frequency, depending on how the medical diagnostic device 50 is to be used. For example, a two (2) megahertz (MHz) or a three (3) MHz signal might be used for obstetric applications to detect fetal heartbeats. A two (2) MHz signal is best suited for detecting fetal heartbeats after the fetus is twelve weeks old and throughout labor and delivery. A three (3) MHz signal has the increased sensitivity needed for the early stages of pregnancy. A five (5) MHz or an eight (8) MHz signal might be used in vascular applications. The five (5) MHz signal is better suited for deep arterial and venous flow detection, while the eight (8) MHz signal can be used for superficial vessel measurements.

The Doppler ultrasound waves propagated by the sender element 90 are directed outward from, and parallel to, the probe 54 and toward the patient being examined. For example, in vascular applications, the detachable nose 60 of the probe 54 is placed next to the patient's P skin over the underlying vessel A, as shown in FIG. 3. In obstetric applications, the detachable nose 60 of the probe 54 is placed next to the woman's W skin on the midline of the abdomen, as shown in FIG. 2. In both vascular and obstetric applications, the ultrasound waves transmitted by the sender element 90 in the detachable nose 60 of the probe 54 are directed toward the flowing blood (not shown).

The flowing blood (not shown) reflects the ultrasound waves and creates a Doppler frequency shift between the frequency of the ultrasound signal 55 from the sender element 90 and the frequency of the reflected ultrasound signal 59. The reflected ultrasound signal 59 is detected and received in the receive element 92, which is also located in the detachable nose 60 of the probe 54. The Doppler frequency shifted electric signal produced by the receive element 92 is an input signal to the Doppler transceiver 94. The Doppler transceiver 94 amplifies the Doppler frequency shifted electric signal and then mixes it with the constant frequency electric sender signal in a heterodyne process to produce the audio frequency electric signal. For convenience, this audio frequency electric signal produced by heterodyning the constant frequency electric sender signal and the Doppler frequency shifted electric signal will be referred to as the Doppler audio signal, understanding that it is an electric, not an acoustic, signal with frequencies in the audio range. The Doppler audio signal has a frequency that is proportional to the velocity of the moving target or flowing blood.

Figure 14:
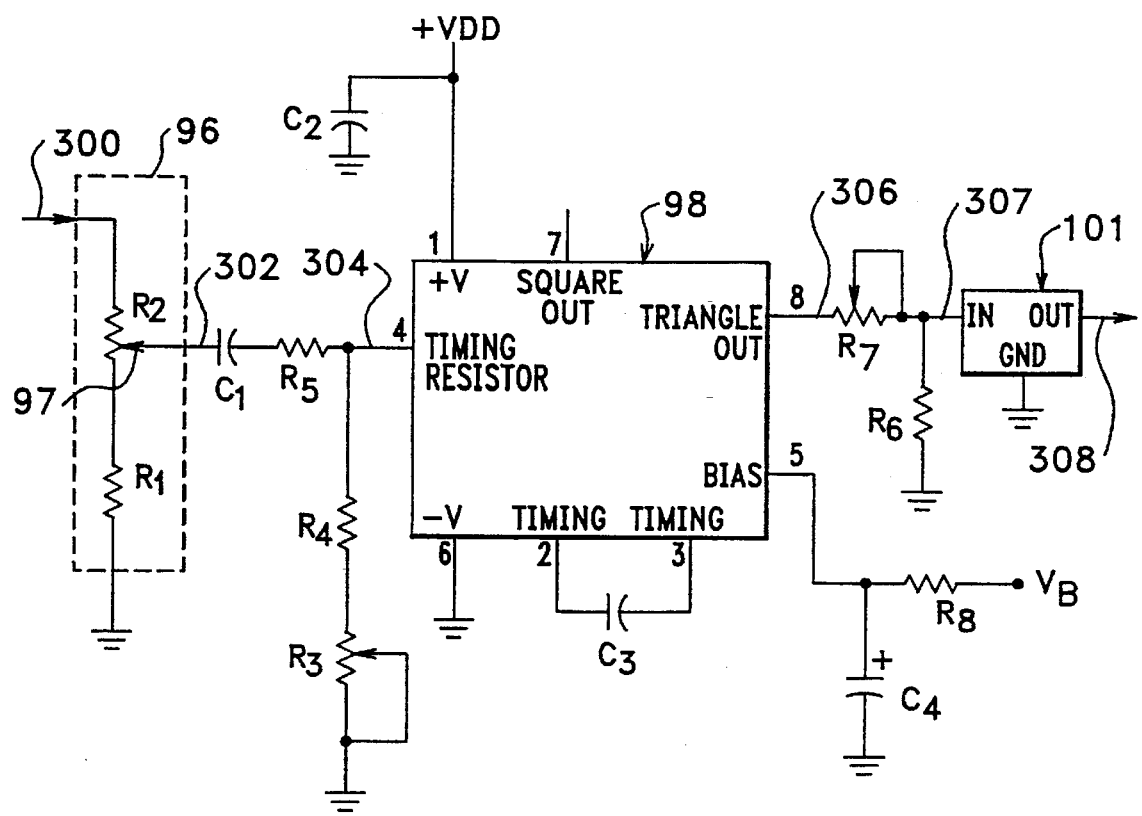
FIG. 14 shows a schematic diagram of the volume control, frequency modulation, and bandpass filter portion of the electronic circuitry of the probe of FIG. 1 constructed to provide the conversion of Doppler audio signal into a sine-wave current signal according to the present invention.

The Doppler audio signal is the output signal from the Doppler transceiver 94 and the input signal to the volume control 96. The volume control 96 is used to attenuate the Doppler audio signal for the purpose of reducing the amplitude and strength of the Doppler audio signal, and to provide the audio volume level preferred by the user. The mount of attenuation done by the volume control 96 is controlled by the user through the operation of a slide potentiometer 97 (see FIGS. 2–5) located on the probe 54. The user adjusts the volume control 96 to produce the desired level of audible output from the speakers 134 in the base unit 52. The volume control 96 is also shown in FIG. 14 and will be discussed in more detail below.

Looking again at FIG. 10, the Doppler audio signal that is the output signal from the Doppler transceiver 94 is also the input signal to the timer control 105. The timer control 105 is used to conserve the energy in the rechargeable battery 107 in the probe 54. The timer control 105 continuously compares the amplitude of the Doppler audio signal to a reference value that is predetermined and preset in the timer control 105. If the amplitude of the Doppler audio signal is below the preset reference value, the timer control 105 initiates a timer clock (not shown) that begins running and runs for a predetermined and preset time. If the Doppler audio signal remains below the preset reference value for the preset time, the timer control 105 provides a signal to the on/off control 106 that turns off the probe 54 and disconnects the rechargeable battery 107 from the remainder of the electronic circuitry in the probe 54. If the amplitude of the Doppler audio signal falls below the preset reference value so as to start the running of the timer clock (not shown), the timer clock (not shown) will be reinitialized if the amplitude of the Doppler audio signal becomes larger than the reference value before the timer clock (not shown) runs for the preset time. Timer clock circuits are well-known to persons having ordinary skill in this art, and thus need not be shown or described in more detail for purposes of this invention.

The output signal from the volume control 96 is the input signal to the frequency modulator 98, which frequency modulates the Doppler audio signal with a 455 kilohertz (KHz) carrier signal. In frequency modulation, a modulating signal is used to vary the frequency of a carrier signal to create a frequency modulated signal. The frequency modulated signal has a constant peak-to-peak amplitude but a varying frequency, where the variation in the frequency of the frequency modulated signal is dependent on the amplitude of the modulating signal. The frequency of the unmodulated carrier signal is called the center frequency. The frequency of the frequency modulated signal varies in a range above and below the center frequency.

Figure 19:
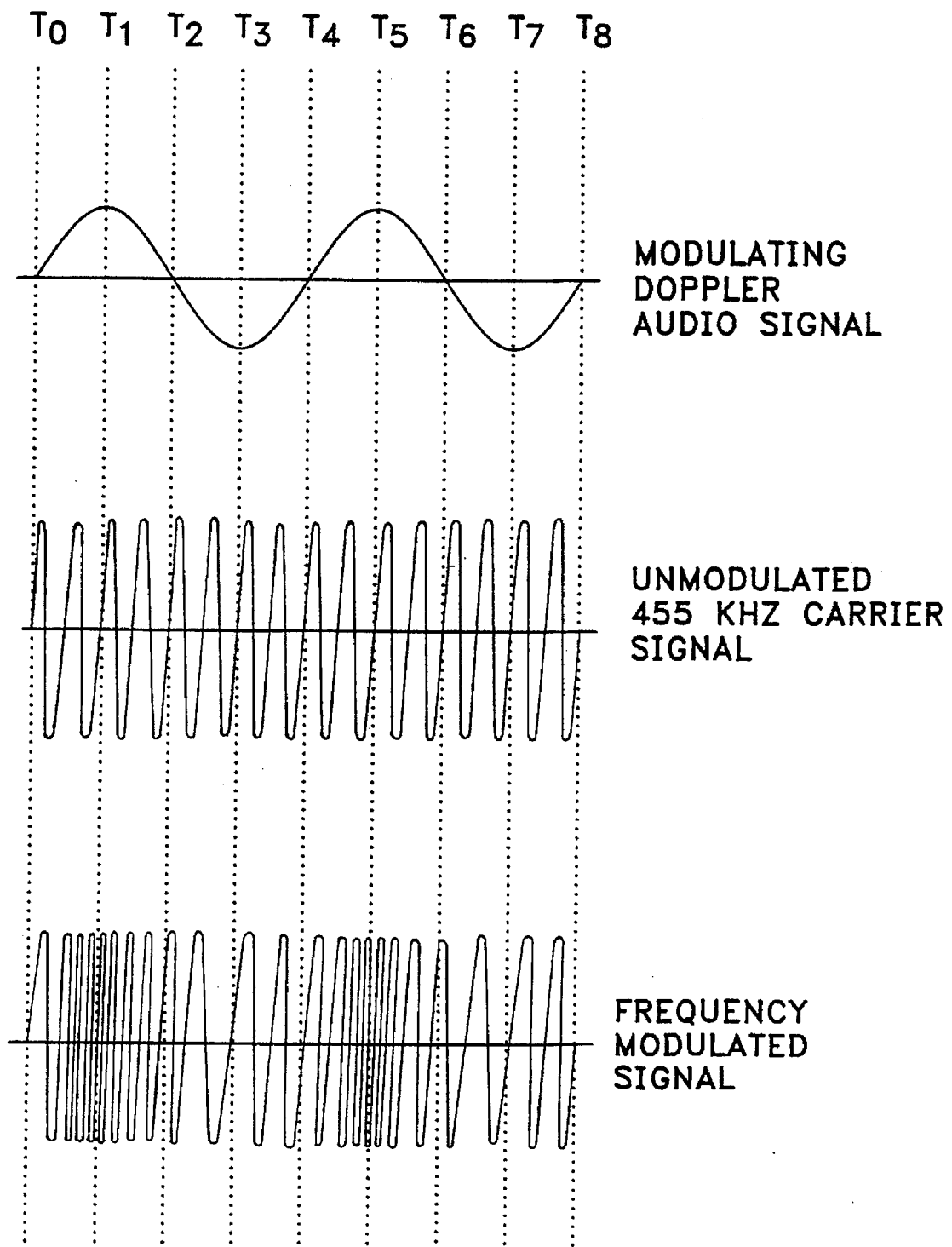
FIG. 19 shows a representation of a modulating signal, a carrier signal, and the resulting frequency modulated signal, as performed in the probe of FIG. 1 according to the present invention.

By way of example and further clarification for the signals involved in the medical diagnostic device 50, the modulating signal is the Doppler audio signal and is shown in FIG. 19. The unmodulated carrier signal has a center frequency of 455 KHz and is shown in FIG. 19. The resulting frequency modulated signal is also shown in FIG. 19. All three signals shown in FIG. 19 will now be discussed in greater detail.

The amount of the amplitude of the modulating Doppler audio signal determines the amount that the unmodulated carrier signal deviates from the center frequency of 455 KHz to produce the frequency modulated signal. For example, at time $T_0$ in FIG. 19, the modulating Doppler audio signal has a zero amplitude. Therefore, the frequency modulated signal is at the center frequency of 455 KHz. As the amplitude of the modulating Doppler audio signal becomes increasingly positive between time $T_0$ and time $T_1$, the frequency of the frequency modulated signal increases above 455 KHz. The frequency modulated signal reaches its maximum frequency when the modulating Doppler audio signal reaches its maximum amplitude at time $T_1$ in FIG. 19. As the amplitude of the modulating Doppler audio signal decreases between time $T_1$ and time $T_2$, the frequency of the frequency modulated signal decreases but remains greater than 455 KHz. At time $T_2$ in FIG. 19, the modulating Doppler audio signal again has a zero amplitude. Therefore, the frequency modulated signal is again at the center frequency of 455 KHz.

As the amplitude of the modulating Doppler audio signal further decreases and becomes negative between time $T_2$ and time $T_3$, the frequency of the frequency modulated signal decreases below 455 KHz. The frequency modulated signal reaches its minimum frequency when the modulating Doppler audio signal reaches its minimum amplitude at time $T_3$ in FIG. 19. As the amplitude of the modulating Doppler audio signal increases between time $T_3$ and time $T_4$, the frequency of the frequency modulated signal increases but remains less than 455 KHz. At time $T_4$ in FIG. 19, the modulating Doppler audio signal again has a zero amplitude. Therefore, the frequency modulated signal is again at the center frequency of 455 KHz.

The frequency of the frequency modulated signal continues to change as the amplitude of the modulating Doppler audio signal continues to increase and decrease. The frequency of the frequency modulated signal returns to the 455 KHz center frequency each time the amplitude of the modulating Doppler audio signal is zero (0).

The rate of the frequency deviation in the frequency modulated signal is determined by the frequency of the modulating Doppler audio signal. For example, if the modulating Doppler audio signal has a frequency of 2 KHz, the frequency of the frequency modulated signal will swing above and below the 455 KHz center frequency of the unmodulated carrier signal two thousand (2,000) times a second. Thus, the frequency of the modulating Doppler audio signal determines the rate of frequency deviation, but not the amount of the frequency deviation. As stated above, the amount of the frequency deviation is determined by the amplitude of the modulating Doppler audio signal.

A 455 KHz carrier signal is chosen because the 455 KHz frequency is generally above the frequencies of the light noise created by incandescent and fluorescent lights, so interference or noise created by such lights can be avoided or filtered out. Furthermore, the 455 KHz frequency falls within the band of frequencies often used in radio receivers, which allows standard and off-the-shelf components to be used in this stage of the signal processing of this invention. In the present invention, the frequency modulation of the 455 KHz carrier signal by the Doppler audio signal will cause the modulated Doppler audio signal to have a frequency between 440 KHz and 470 KHz. The 15 KHz limit on the variance from 455 KHz is caused by the limits placed on the amplitude of the Doppler audio signal by the Doppler transceiver 94. The output signal of the frequency modulator 98 is a frequency modulated voltage signal, where the amount of frequency modulation is based on the amplitude of the Doppler audio signal input from the volume control 96. Frequency modulators and frequency modulation of a carrier signal with an audio signal are well known to persons having ordinary skill in the art. For example, the XR-2209 Precision Oscillator manufactured by Exar Corporation of San Jose, Calif., can be used in this invention as the frequency modulator 98. The frequency modulator 98 and its supporting electronic circuitry are shown in FIG. 14 and will be discussed in more detail below.

Looking again at FIG. 10, the output signal from the frequency modulator 98 is the input signal to the bandpass filter 101. The bandpass filter 101 is centered at 455 KHz and passes electric signals having frequencies between 440 KHz and 470 KHz. The bandpass filter 101 attenuates and filters out any electric signals or noise having frequencies below 440 KHz and electric signals or noise having frequencies above 470 KHz. The bandpass filter 101 is used to filter out unwanted signals or noise that did not originate from the reflected Doppler signal and to filter out harmonic signals which may be present on the output signal from the modulator 98. Bandpass filters are often used in AM and FM commercial radios and are well known to persons having ordinary skill in the art. For example, the SFG455B Ceramic Filter manufactured by muRata Erie of Smyrna, Ga., can be used in this invention for the bandpass filter 101. The bandpass filter 101 is shown in FIG. 14 and will be discussed in more detail below.

Looking again at FIG. 10, the output signal from the bandpass filter 101 is the input signal to the voltage-to-current converter 102. A significant feature of this invention includes the voltage-to-current converter 102, which converts the voltage-based and frequency modulated input signal to a current-based and frequency modulated output signal that flows through and drives the six infrared light emitting diodes (LEDs) 104 $LED_1$, $LED_2$, $LED_3$, $LED_4$, $LED_5$ and $LED_6$ (see FIGS. 4–6) located on the probe 54. Consequently, according to this invention, the frequency of the infrared light signal output of the six infrared LEDs 104 $LED_1$, $LED_2$, $LED_3$, $LED_4$, $LED_5$ and $LED_6$ can have a specific relationship with the Doppler audio signal, as will be discussed in more detail below. The six LEDs 104 $LED_1$, $LED_2$, $LED_3$, $LED_4$, $LED_5$ and $LED_6$, are sized, shaped, and positioned in the probe 54 in a manner that maximizes multidirectional or global broadcasting of the infrared carrier medium of the Doppler audio signal to enhance the likelihood that it will reach and be received by the base unit 52 uninterrupted.

Figure 5:
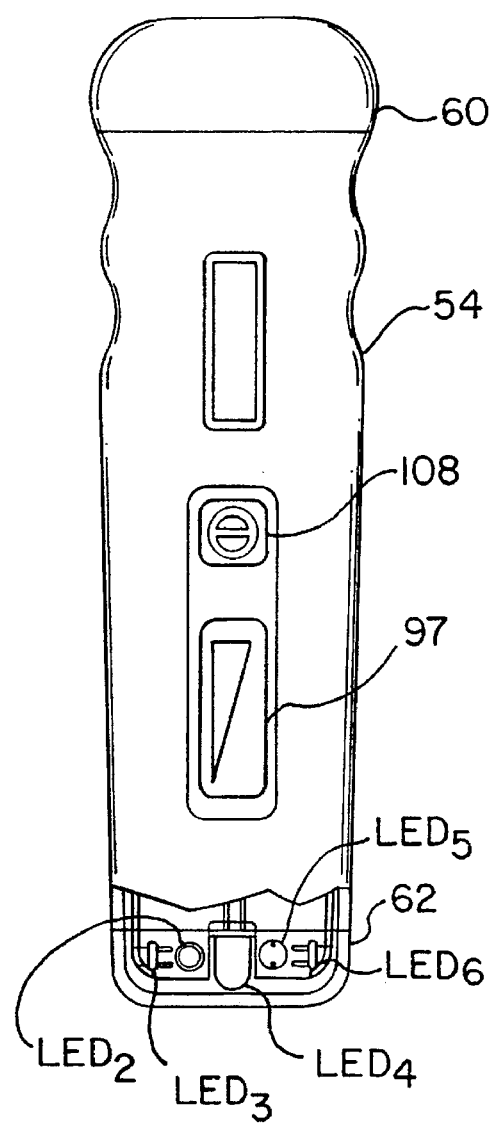
FIG. 5 shows a top view of the ultrasound probe of the medical diagnostic device of FIG. 1.
Figure 6:
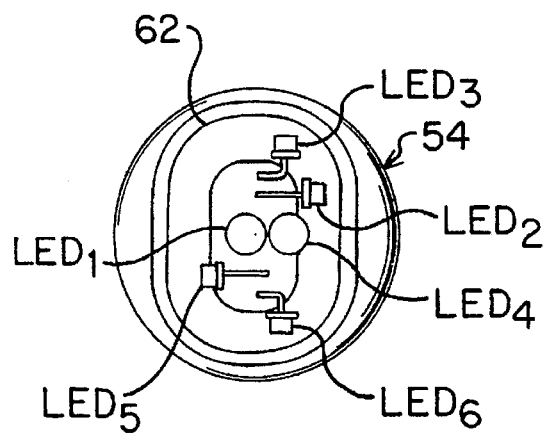
FIG. 6 shows an end view of the ultrasound probe of the medical diagnostic device of FIG. 1 illustrating the orientation and placement of the infrared light emitting diodes.

The LEDs 104 are located at the end 62 of the probe opposite the detachable nose 60, as shown in FIGS. 4, 5, and 6. Furthermore, the six infrared LEDs 104 are positioned so that two ($LED_1$, $LED_4$) of the infrared LEDs 104 emit infrared light in a direction outward and parallel to the longitudinal center axis of the probe 54. The four ($LED_2$, $LED_3$, $LED_5$, $LED_6$) remaining infrared LEDs 104 are positioned in approximately the same plane so that they emit infrared light outward from, and perpendicular to, the probe 54. Furthermore, each of the four remaining infrared LEDs 104 $LED_2$, $LED_3$, $LED_5$, and $LED_6$ emits infrared light in a direction that is either ninety degrees (90°) or one hundred eighty degrees (180°) apart from the direction of each of the other three. As previously discussed, with this configuration of the six infrared LEDs 104 $LED_1$, $LED_2$, $LED_3$, $LED_4$, $LED_5$, and $LED_6$, the infrared light signals emitted by the six infrared LEDs 104 $LED_1$, $LED_2$, $LED_3$, $LED_4$, $LED_5$, and $LED_6$ are transmitted in a plurality of directions. The light signals will reflect off the walls, ceiling, equipment, and other objects in the room where the medical diagnostic device 50 is being used. Having the six infrared LEDs 104 $LED_1$, $LED_2$, $LED_3$, $LED_4$, $LED_5$, and $LED_6$ oriented in different directions at the end 62 of the probe 54 ensures that at least one of the infrared light signals emitted by the six infrared LEDs 104 $LED_1$, $LED_2$, $LED_3$, $LED_4$, $LED_5$, and $LED_6$ will be detected by the photodetectors 120 $DET_1$, $DET_2$, $DET_3$, and $DET_4$ located on the base unit 52.

Figure 15:
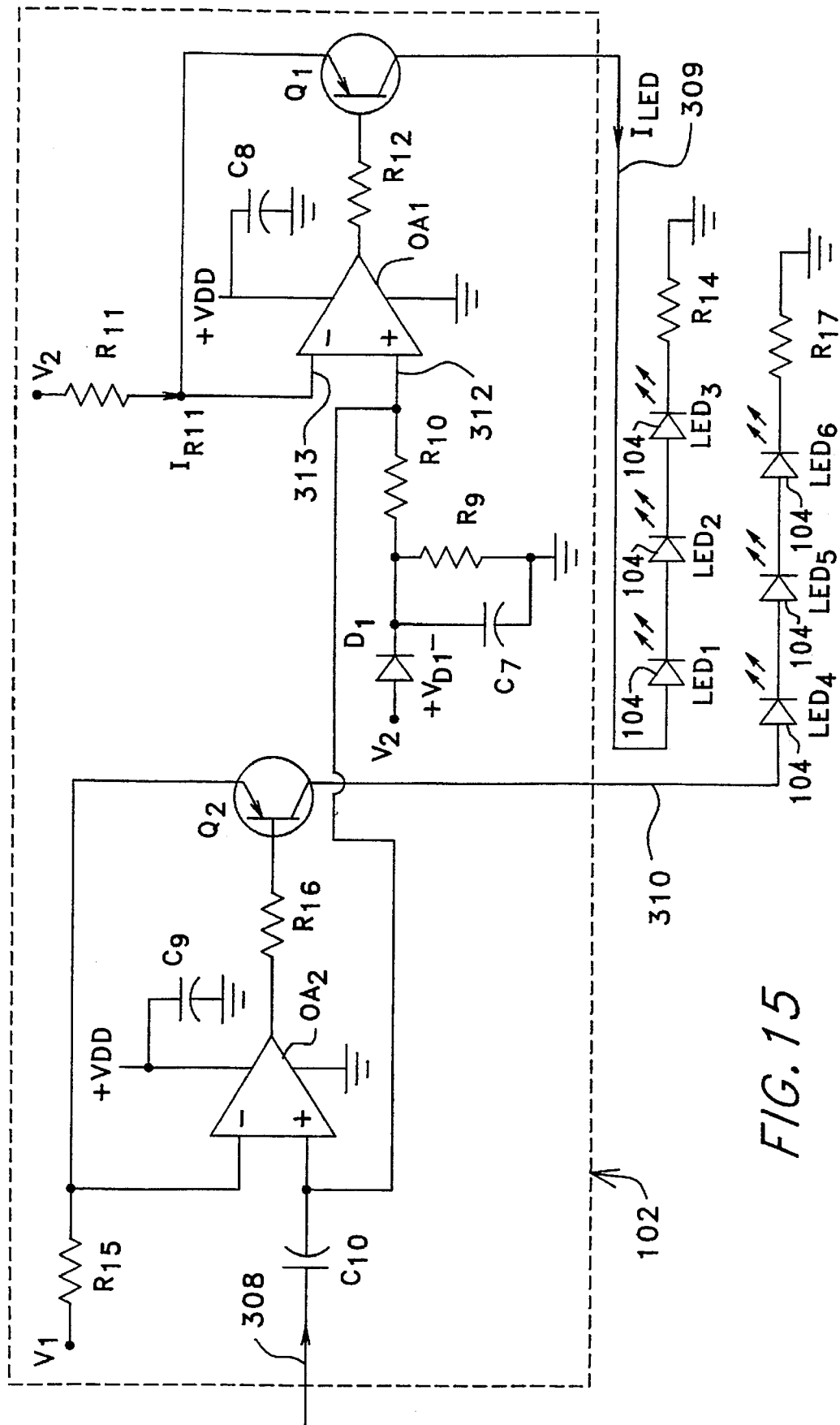
FIG. 15 shows a schematic diagram of the voltage-to-current converter portion of the electronic circuitry of the probe of FIG. 1 constructed to convert an input voltage signal into an output current signal according to the present invention.

The voltage-to-current converter 102 follows a linear relationship when converting the voltage levels of its input signal to the current levels of its output signal. A current-based signal is better suited than a voltage-based signal to drive the six infrared LEDs 104, $LED_1$, $LED_2$, $LED_3$, $LED_4$, $LED_5$ and $LED_6$, because the amount of light emitted by each of the six infrared LEDs 104 $LED_1$, $LED_2$, $LED_3$, $LED_4$, $LED_5$ and $LED_6$ depends entirely on the current flowing through it, and the voltage-to-current ratio in a LED is very nonlinear. Therefore, using the voltage-to-current converter 102 before driving the six infrared LEDs 104 $LED_1$, $LED_2$, $LED_3$, $LED_4$, $LED_5$ and $LED_6$, ensures that the amount or intensity of infrared light emitted by the LEDs 104 $LED_1$, $LED_2$, $LED_3$, $LED_4$, $LED_5$ and $LED_6$ will vary in a linear relationship with the voltage level of the input signal to the voltage-to-current converter 102. If the voltage-to-current converter 102 was not used, and the output signal from the bandpass filter 98 was passed directly to the six infrared LEDs 104 $LED_1$, $LED_2$, $LED_3$, $LED_4$, $LED_5$ and $LED_6$, the amount or intensity of the infrared light emitted by the six infrared LEDs 104 $LED_1$, $LED_2$, $LED_3$, $LED_4$, $LED_5$ and $LED_6$ would vary in a nonlinear relationship with the voltage level of the input signal to the six infrared LEDs 104 $LED_1$, $LED_2$, $LED_3$, $LED_4$, $LED_5$ and $LED_6$. The OEDEL-1L1 infrared light emitting diode manufactured by Lumex of Palatine, Illinois, can be used in this invention for $LED_1$ and $LED_4$. The SFH-487P infrared light emitting diode manufactured by Siemens Components, Inc., of Cupertino, Calif. can be used in this invention for $LED_2$, $LED_3$, $LED_5$, and $LED_6$. The electronic circuitry for the voltage-to-current converter 102 is shown in FIG. 15 and will be discussed in more detail below.

Looking at FIGS. 4 and 5, the components of the base unit 52 will now be discussed in greater detail. The user activates the base unit 52 by momentarily pressing the on/off switch 152 to place the on/off control 150 into the "on" state. Placing the on/off control 150 into the "on" state provides connection between the rechargeable battery 154 in the base unit 52 and the remainder of the electronic circuitry located in the base unit 52. The user deactivates the base unit 52 by momentarily pressing the on/off switch 152 again to place the on/off control 150 into the "off" state. Placing the on/off control 150 into the "off" state by momentarily pressing the on/off switch 152 disconnects the rechargeable battery 154 in the base unit 52 from the remainder of the electronic circuitry located in the base unit 52.

As discussed above, the on/off control 150 provides connection between the battery 154 and the power supplies 156 when the on/off control 150 is in the "on" state. The power supplies 156 take the voltage supplied by the rechargeable battery 154 and convert it to create the necessary voltages and voltage levels used by the electronic components in the electronic circuitry in the base unit 52. The ten V170R cells manufactured by Varta Batteries, Inc., can be used in the rechargeable battery 154 in the base unit 52. The use of power supplies and power supply circuity to create different voltage levels is well known to people having ordinary skill in the art and need not be shown or described in more detail.

The battery 154 in the base unit 52 is rechargeable. The recharger 158 is used along with the charge circuit 160 to recharge the rechargeable battery 154 in the base unit 52. When the base unit 52 is properly positioned (not shown) in the recharging stand 56, and the recharger 158 is plugged into an electrical outlet (not shown), the recharger 158 drives the charge circuit 160 in the base unit 52 to recharge the rechargeable battery 154 in the base unit 52. Likewise, the recharger 158 is used along with the charge circuit 164 to recharge the rechargeable battery 107 in the probe 54. When the probe 54 is correctly positioned in the probe holder 57 in the base unit 52 (see FIGS. 1 and 9), the base unit 52 is positioned in the recharging stand 56, and the recharger 158 is plugged into an electrical outlet (not shown), the recharger 158 drives the charge circuit 164 to recharge the rechargeable battery 107 in the probe 54. The use of recharging circuitry and rechargeable batteries is well known to people having ordinary skill in the art and need not be shown or described in further detail for purposes of this invention.

The user of the medical diagnostic device 50 uses the select controller 170 and the select switch 172 to signal the microcontroller 146 that the medical diagnostic device 50 is operating in the obstetrical mode or in the vascular mode. The user of the medical diagnostic device 50 selects either the obstetrical function or the vascular function through the select controller 170 by pressing the select switch 172 to select either the vascular position (not shown) or the obstetrical position (not shown) for the purpose or advantages described above. Alternately pressing the select switch 172 causes the select controller 170 to provide an signal to the microcontroller 146 alternately indicating that the obstetrical function or the vascular function has been chosen by the user. Depending on whether the vascular mode or the obstetric mode is indicated by the select controller 170, the microcontroller 146 processes either the vascular waveform signal obtained from the vascular converter 140 or the fetal heart rate waveform signal obtained from the fetal heart rate generator 142. The microcontroller also provides a visual display signal to the display driver 186 which provides a digital signal to the digital display 188 on the base unit 52.

The microcontroller 146 is a standard off-the-shelf microprocessor. For example, the 80196 manufactured by the Intel Corporation of Santa Clara, Calif., can be used in this invention for the microcontroller 146. The microcontroller 146 has an associated memory 182 and an associated voltage reference 184. The memory 182 is used to store the program and software data used in the microcontroller 146. The voltage reference 184 is used to set the amplitude of the signals presented to the ADC 200 from the vascular heart rate converter 140 and the fetal heart rate generator 142. The voltage reference 184 sets the scale of the digital output of the ADC 200. Full scale output of the ADC 200 is equal to voltage reference value from voltage reference 184.

The operational block diagram for the electronic circuitry in the base unit 52, which receives and processes the frequency modulated sine wave infrared light signals emitted by the LEDs 104 $LED_1$, $LED_2$, $LED_3$, $LED_4$, $LED_5$ and $LED_6$, is shown in FIGS. 4 and 5. Looking at FIG. 11, the infrared light signals emitted by the six infrared LEDs 104 $LED_1$, $LED_2$, $LED_3$, $LED_4$, $LED_5$ and $LED_6$ on the probe 54 are detected by one or more of the photodetectors 120 $DET_1$, $DET_2$, $DET_3$, and $DET_4$ located on the base unit 52 (see FIGS. 7-9). The photodetectors 120 $DET_1$, $DET_2$, $DET_3$, and $DET_4$, are each capable of detecting and converting the infrared light signals to electric signals, which still carry the Doppler audio signals produced in the probe 54, as described above.

Figure 9:
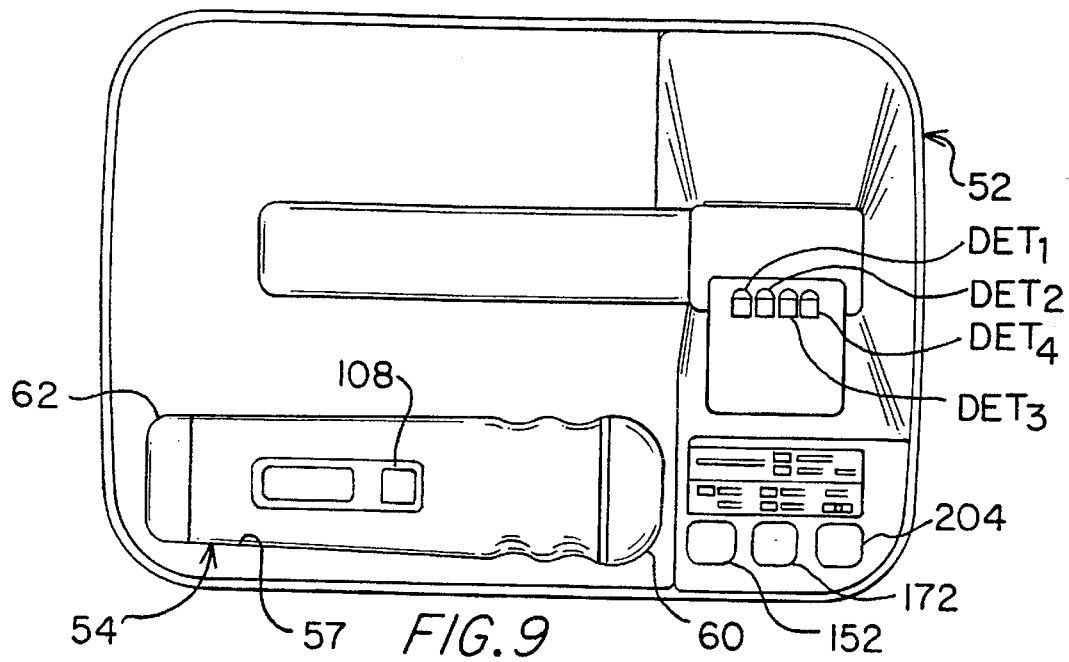
FIG. 9 shows a top view of the base unit and the probe of the medical device of FIG. 1, illustrating the position orientation of the photodetectors and the position of the probe when the probe is nested within the base unit.
Figure 7:
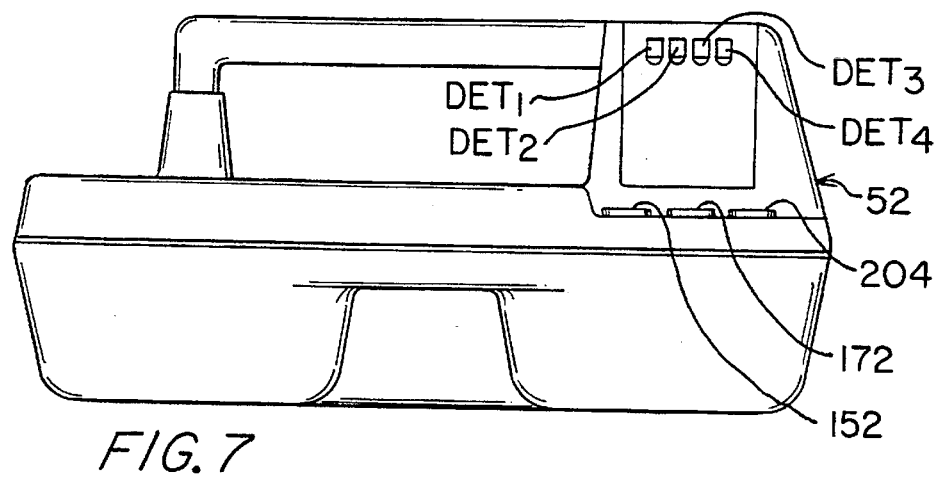
FIG. 7 shows a side view of the base unit of the medical diagnostic device of FIG. 1, illustrating the position and orientation of the photodetectors.
Figure 8:
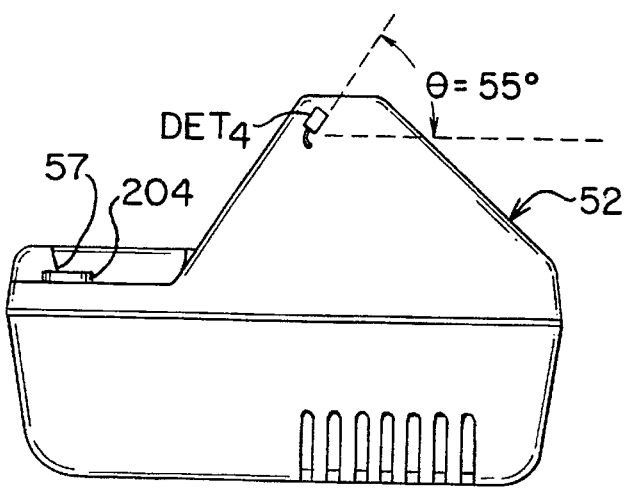
FIG. 8 shows an end view of the base unit of the medical diagnostic device of FIG. 1, illustrating the position and orientation of the photodetectors.

The frequency modulated infrared light signals emitted by the LEDs 104 $LED_1$, $LED_2$, $LED_3$, $LED_4$, $LED_5$ and $LED_6$ on the probe 54 have a frequency that varies between 440 KHz and 470 KHz. Therefore, the output electric signals from the photodetectors 120 $DET_1$, $DET_2$, $DET_3$, and $DET_4$ also have a frequency that varies between 440 KHz and 470 KHz. The photodetectors 120 $DET_1$, $DET_2$, $DET_3$, and $DET_4$ are positioned on the base unit 52 so as to ensure that the frequency modulated infrared light signals emitted by the six infrared LEDs 104 $LED_1$, $LED_2$, $LED_3$, $LED_4$, $LED_5$ and $LED_6$ are either directly detected by the photodetectors 120 $DET_1$, $DET_2$, $DET_3$, and $DET_4$ or are detected by the photodetectors 120 $DET_1$, $DET_2$, $DET_3$, and $DET_4$ after the infrared light signals reflect off of the walls, the ceiling, or other objects in the room where the medical diagnostic device 50 is being used. This is accomplished by positioning the photodetectors 120 $DET_1$, $DET_2$, $DET_3$, and $DET_4$ on the base unit 52 such that the active surfaces of the photodetectors 120 $DET_1$, $DET_2$, $DET_3$, and $DET_4$ are aligned to intercept infrared light from a wide variety of angles, including both the horizontal and the vertical planes, as shown in FIGS. 7-9. The SFH205 photodetectors manufactured by Siemens Components, Inc., of Cupertino, Calif., can be used as the photodetectors 120 $DET_1$, $DET_2$, $DET_3$, and $DET_4$ in this invention.

Figure 16:
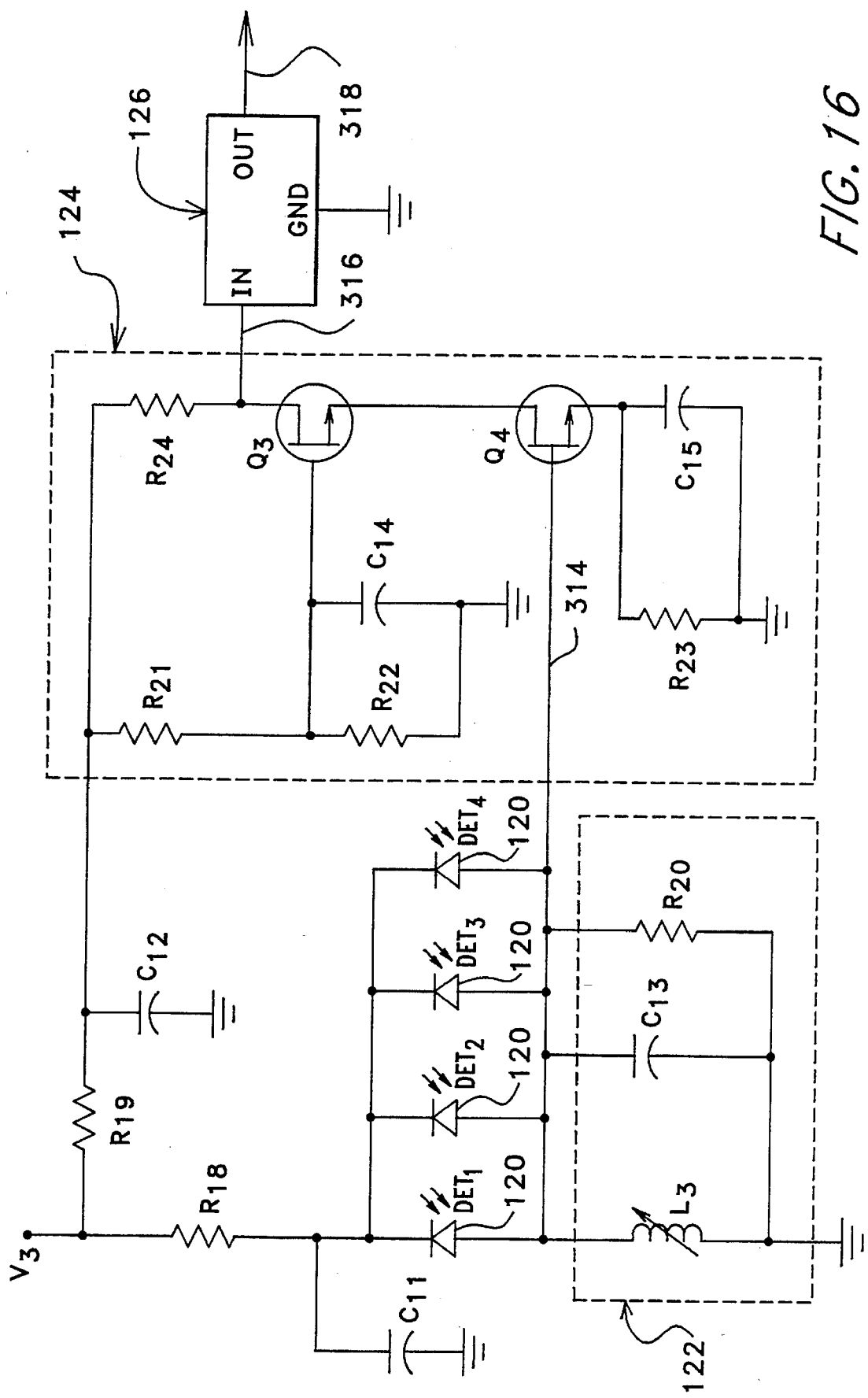
FIG. 16 shows a schematic diagram of the light detector, resonant circuit, preamplifier, and bandpass filter portion of the electronic circuitry of the base unit of FIG. 1 constructed to provide the detection, preamplification, and filtering functions of the infrared light signal emitted by the light emitting diodes according to the present invention.

The infrared light signals detected by the photodetectors 120 $DET_1$, $DET_2$, $DET_3$, and $DET_4$ create electric signals in which the current varies linearly with the amplitude or intensity of the infrared light signal emitted by the LEDs 104 $LED_1$, $LED_2$, $LED_3$, $LED_4$, $LED_5$ and $LED_6$ detected by the photodetectors 120 $DET_1$, $DET_2$, $DET_3$, and $DET_4$. The output electric signals from the photodetectors 120 $DET_1$, $DET_2$, $DET_3$, and $DET_4$ are the input signals to the resonant circuit 122, which converts the current output of the photodetectors 120 $DET_1$, $DET_2$, $DET_3$, and $DET_4$ into a voltage, which is the input signal to the preamplifier 124. In addition, the resonant circuit 122 limits the bandwidth of the electric signal provided to the preamplifier 124. The resonant circuit 122 and its supporting electronic circuitry are shown in FIG. 16 and will be discussed in more detail below.

The frequency modulated electric output signal from the resonant circuit 122 is the input signal to the preamplifier 124, which amplifies the electric signal to strengthen it by adding more power before proceeding to additional signal processing components. The output signal from the preamplifier 124 is the input signal to the bandpass filter 126. The bandpass filter 126 attenuates and filters electric signals having frequencies below 440 KHz and electric signals having frequencies above 470 KHz. The bandpass filter 126 is used to filter out unwanted signals that did not originate from the six infrared LEDs 104 $LED_1$, $LED_2$, $LED_3$, $LED_4$, $LED_5$ and $LED_6$ on the probe 54 that are detected by the photodetectors 120 $DET_1$, $DET_2$, $DET_3$, and $DET_4$, and to filter out electric noise signals that may be created by the base unit 52 or by lights and equipment located where the medical diagnostic device 50 is being used. In addition, the bandpass filter circuit 126 cleans up the signal by removing extraneous frequencies or noise that may have produced in the preamplifier circuit 124. The SFG455B Ceramic Filter manufactured by muRata Erie of Smyrna, Ga., can be used in this invention for the bandpass filter 126. The bandpass filter 126 and its supporting electronic circuitry are shown in FIG. 16 and will be discussed in more detail below.

Figure 17:
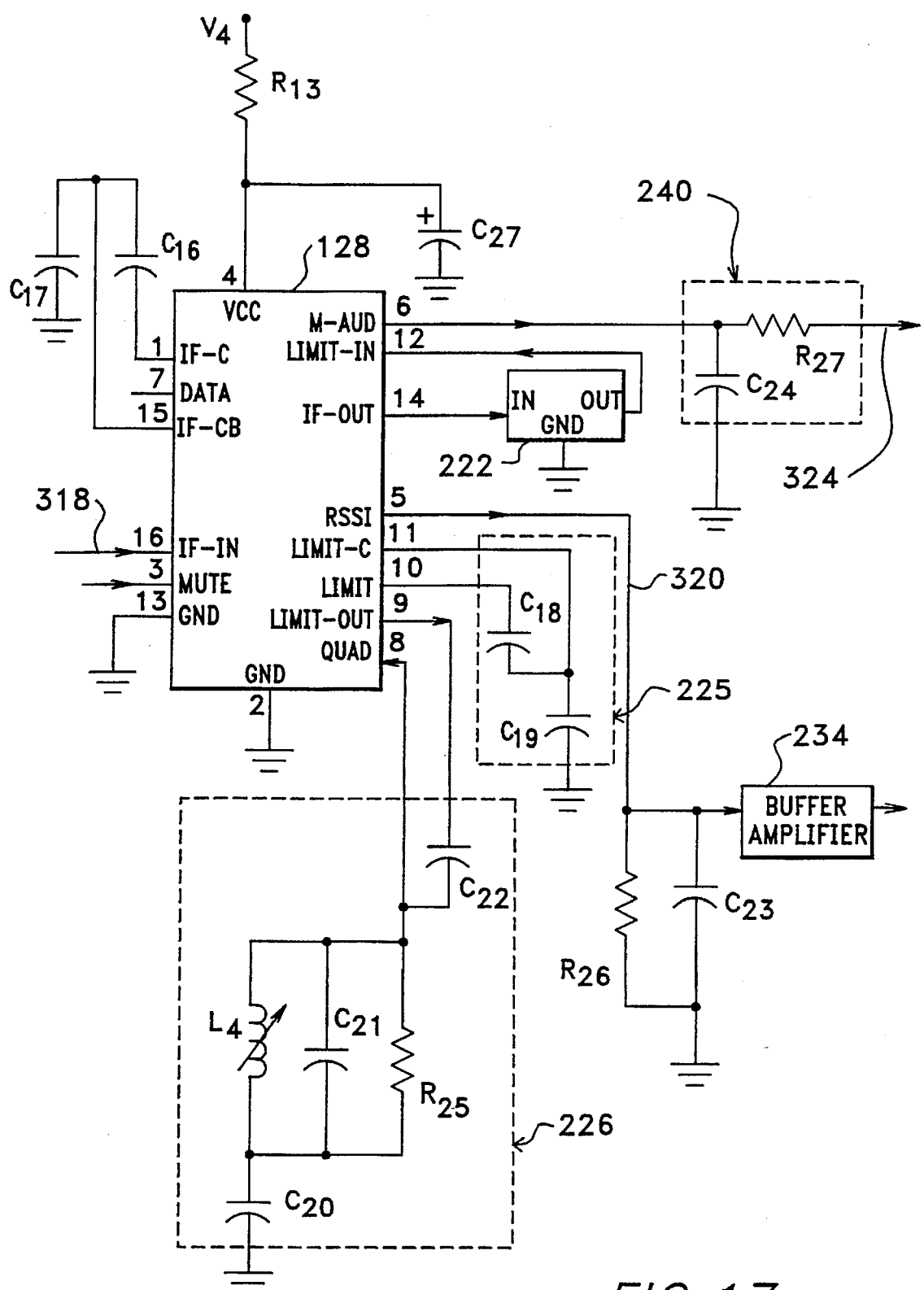
FIG. 17 shows a schematic diagram of the demodulation and filtering portion of the electronic circuitry of the base unit of FIG. 1 constructed to provide the Doppler audio signal recovery functions of the base unit according to the present invention.

The output signal from the bandpass filter 126 is the input signal to the frequency demodulator 128. The frequency demodulator 128, which may be an integrated circuit (IC), amplifies, demodulates, and filters the Doppler audio signal encoded within the frequency modulated infrared light signal detected by the photodetectors 120. Frequency demodulators are well known by people having ordinary skill in the art. For example, the NE/SA604A High-Performance Low-Power FM IF System manufactured by the Phillips (formerly the Signetics Company) of Sunnyvale, Calif., can be used in this invention for the frequency demodulator 128. The output signal from the frequency demodulator 128 is an electric signal that varies in amplitude and frequency and the frequency of the output signal is in the audio range, that is, the frequency of the output signal is between 100 Hertz and one (1) KHz. In general terms, the output signal of the frequency demodulator 128 represents the Doppler audio signal discussed above, which was the input signal to the frequency modulator 98 in the probe 54. Therefore, the output signal from the frequency demodulator 128 is the recovered Doppler audio signal, which was provided by the Doppler transceiver 94 and volume control 96 in the probe 54. In more specific terms, the output signal from the frequency demodulator 128 is an electric signal that has a frequency that is a function of the rate of change of the frequency of input signal to the frequency demodulator 128, and it has an amplitude that is a function of the instantaneous deviation of the frequency of the input signal to the frequency demodulator 128 from 455 KHz. The output signal from the frequency demodulator 128 is the Doppler audio signal that was the output signal from the Doppler transceiver 94. The frequency demodulator 128 and its supporting electronic circuitry are shown in FIG. 17 and will be discussed in more detail below.

The Doppler audio output signal from the frequency demodulator 128 is the input signal to the Doppler audio controller 130. The Doppler audio controller 130 includes a low pass filter that further smooths the signal created by the frequency demodulator 128 and eliminates high frequencies that might be included in the electric signal generated by the frequency demodulator 128. The Doppler audio controller 130 also amplifies the signal with an amplifier after the signal passes through the low pass filter and then filters the signal with a high-pass filter to remove signals created by extraneous movement of the probe 54. Audio controllers are well known in the art.

The output signal from the Doppler audio controller 130 is the input signal to the audio power amplifier 132, the tape recorder connector 138, the vascular converter 140, and the fetal waveform generator 142. The audio power amplifier 132 amplifies the Doppler audio signal so that the Doppler audio signal can be converted to acoustic sound waves and broadcast by the speakers 134 located in the base unit 52 or through headphones (not shown) connected to the base unit 52 though the headphone connector 136. The audio power amplifier 132 is a standard audio signal power amplifier and its use is well known to persons having ordinary skill in the art. For example, the TDA7052 manufactured by Phillips (formerly the Signetics Company) of Sunnyvale, Calif., can be used in this invention for the audio power amplifier 132. The amplified signal output from the audio power amplifier 132 is the input signal to both the speakers 134 located in the base unit 52 and the headphone connector 136 located in the base unit 52. A standard headphone (not shown) can then be plugged into the headphone connector 136 and used with the medical diagnostic device 50. The tape recorder connector 138 provides a standard connection to a tape recorder (not shown) so that the Doppler audio signal can be recorded and stored.

The vascular converter 140 converts the Doppler audio signal from the Doppler audio controller 130 into a signal representing the Doppler audio signal and thus, the vascular heart rate of the patient being monitored. The vascular converter 140 converts the Doppler audio signal to the vascular waveform by the use of a frequency-to-voltage converter whose DC output voltage varies linearly with the average frequency of the input signal to the vascular converter 140 for the purpose of representing the complex audio signal with a relatively simple low frequency waveform. The use of frequency-to-voltage converters are well known to people having ordinary skill in the art. For example, the LM2907 manufactured by National Semiconductor, Inc., can be used for the vascular converter 140 in this invention. The vascular waveform output signal from the vascular converter 140 is an input signal to the microcontroller 146, as shown in FIG. 12.

The fetal heart rate generator 142 converts the Doppler audio signal from the Doppler audio controller 130 into a fetal waveform signal that is representative of fetal heart rate of the baby of the pregnant woman W being monitored. The fetal heart rate generator 142 converts the Doppler audio signal to the fetal waveform signal in the following steps. First, the amplitude of the Doppler audio signal is adjusted to a predetermined level by an automatic gain control. The automatic gain control holds the average of the amplitude of the Doppler audio signal at a constant level. The output of the automatic gain control is the input to an envelope detector which converts the Doppler audio signal into a waveform comprised of a DC voltage which varies linearly with the amplitude of the Doppler audio signal. The waveform signal from the envelope detector is amplified and passed through a low pass filter which further smooths the waveform. The function, design, and operation of the fetal heart rate converter 142 are well known to persons having ordinary skill in the art. The fetal waveform output signal from the fetal heart rate generator 142 is an input signal to microcontroller 146, as shown in FIG. 12.

The microcontroller 146 includes an analog-to-digital converter (ADC) 200 that converts either the vascular waveform signal from the vascular converter 140 or the fetal waveform signal from the fetal heart rate generator 142 into a twelve bit digital output signal. The twelve bit output signal is scaled into a four bit signal which preserves enough accuracy to determine the heart rate accurately and enables the heart rate calculations to be completed quickly. The analog-to-digital conversion done by ADC 200 in the microcontroller 146 is controlled completely by software.

After the microcontroller 146 converts either the analog input signal from the vascular converter 140 or the analog signal from the fetal heart rate generator 142 into a digital signal, the output digital signal from the ADC 200, corresponding to either the vascular waveform from the vascular generator 140 or the fetal waveform from the fetal heart rate generator 142, becomes the input signal to the heart rate calculator 202 in the microcontroller 146. The output of the select controller 170 determines which digital signal in the ADC 200 becomes the input signal to the heart rate calculator 202.

The function of the heart rate calculator 202 is performed completely in software in the microcontroller 142. The heart rate calculator 202 takes the digital input signal from the ADC 200 and calculates the corresponding heart rate associated with the digital signal. Standard and well known mathematical techniques such as, for example, techniques using autocorrelation functions or modulus difference functions performed on a set of data samples, can be used to determine the period of the digital signal. Once the period of the digital signal is determined, a conversion to heart beats per minute can be easily made, as is well known in the art.

The heart rate calculator 202 also has an input from the heart rate average switch 204. When the user momentarily presses the heart rate average switch 204, the heart rate calculator 202 calculates the average heart rate from the digital data gathered during the previous three (3) seconds. The average heart rate is displayed for ten (10) seconds and the heart rate calculator 202 then returns to sending the current heart rate to the display driver 186. The voltage $V_S$ supplied to the heart rate selector switch 204 is provided by the power supplies 156 and can be, for example, 5.0 volts.

The output signal from the heart rate calculator 202 is the input signal to the display driver 186 which is used to drive the three digit heart rate LED display 188 located on the base unit 52. The use of a microcontroller to drive a LED display is well known to people having ordinary skill in the art.

More detailed exemplary schematic diagrams for the significant parts of the electronic circuitry in the medical diagnostic device 50 are shown in FIGS. 7–11. In describing and discussing the electronic components, the standard symbols will be used. For example, "R" will be used for resistors, "C" will be used for capacitors, "L" will be used for inductors, "D" will be used for diodes, "Q" will be used for transistors, "OA" will be used for operational amplifiers, "V" will be used for voltages, and "I" will be used for currents.

The electronic components and the electronic circuitry for the volume control 96, the frequency modulator 98, and the bandpass filter 101 are shown schematically in FIG. 14. The volume control 96, which receives the Doppler audio signal on lead 300, includes a fixed value resistor $R_1$ for setting the minimum voltage level and a variable resistor $R_2$ for varying the voltage level. The value for the variable resistor $R_2$ is controlled by the user through the operation of the slide potentiometer 97 located on the probe 54 (see FIGS. 2–5).

The user can adjust the slide potentiometer 97 to increase or decrease the voltage level of the output signal from the volume control 96 on lead 302.

The output signal of the volume control 96 on lead 302 is the input signal of the frequency modulator 98 on lead 304. As discussed above, frequency modulator 98 uses the signal from the volume control 96 to frequency modulate a carrier signal. The carrier signal can be any convenient frequency for purposes of this invention, but a frequency of 455 KHz is preferred for the reasons described above. In the resulting frequency modulated (FM) output signal from the frequency modulator 98 on lead 306, the deviation of the instantaneous frequency of the output signal from the frequency of the carrier signal is directly proportional to the instantaneous amplitude of the input signal on lead 304 to the frequency modulator 98. As discussed above, the XR-2209 Precision Oscillator 98 manufactured by Exar Corporation of San Jose, Calif., can be used as the frequency modulator function. The electrical specifications and the operational characteristics for the Exar XR-2209 Precision Oscillator are provided in the Exar Databook, copyrighted 1992. In the electronic circuit for the frequency modulator 98 shown in FIG. 14, the capacitor $C_1$ acts as a DC block to eliminate external DC voltages on the input lead 304 to the frequency modulator 98. The capacitor $C_2$ acts as an AC filter to ground for the required supply voltage $V_{DD}$ so that high frequency signals are not supplied to the frequency modulator 98. The voltage $V_{DD}$ is supplied by the power supplies 109 in the probe 54 (see FIG. 10) and can be, for example, 12 volts. The variable resistor $R_3$ and the fixed value resistors $R_4$ and $R_5$, along with the capacitor $C_3$, set the frequency of the carrier signal of the frequency modulator 98 to the desired frequency, such as 455 Khz. The fixed value resistor $R_8$ and the capacitor $C_4$ are used to supply the necessary bias voltage $V_B$ to the frequency modulator 98. The bias voltage $V_B$ is supplied by the power supplies 109 in the probe 54 (see FIG. 10), and can be, for example, 5.5 volts. The output from the frequency modulator 98 is amplitude adjusted by the fixed value resistor $R_6$ and the variable resistor $R_7$ configured in a classic voltage divider configuration. The variable resistor $R_7$ is preferably preset so that the peak-to-peak voltage of the output signal on lead 306 from the frequency modulator 98 is two times $V_{D1}$, the voltage drop across the diode $D_1$ shown in FIG. 15. The diode $D_1$ and the voltage $V_{D1}$ will be discussed in more detail below.

It is desirable to have the frequency modulated output signal from the frequency modulator 98 be a sine wave, because sine wave signals do not produce harmonic frequencies and therefore create fewer high frequency signals that might cause interference with the Doppler transceiver 94 or other equipment located where the medical diagnostic device 50 is being used. The Exar XR-2209 Precision Oscillator 98, however, creates only a frequency modulated square wave output voltage signal or a frequency modulated triangle wave output voltage signal, both of which may contain harmonic sine wave signals. The triangle wave frequency modulated output signal from the precision oscillator 98 is chosen for this invention because a triangle wave is closer to a sine wave than is a square wave, and subsequent circuit components described below are used to convert the triangle wave output on lead 306 to a sine wave. Therefore, the output from the frequency modulator 98 on lead 306 is preferably, but not necessarily, a triangle wave voltage signal whose carrier frequency of 455 KHz is frequency modulated to as much as plus or minus 15 KHz by amplitude of the voltage in the Doppler audio signal from the volume control 96. Therefore, the output signal from the frequency modulator 98 on lead 306 is preferably a frequency modulated triangle wave voltage signal that has a center frequency of 455 KHz, whose frequency varies between 440 KHz and 470 KHz, and that has an amplitude that varies between plus $V_{D1}$ volts and minus $V_{D1}$ volts. The frequency of the triangle wave output voltage signal from the frequency modulator 98 on lead 306 varies as a function of the amplitude of the voltage of the input Doppler audio signal to the frequency modulator 98.

The output signal from the frequency modulator 98 on lead 306 is the input signal to the bandpass filter 101 on lead 307 which is used to filter out unwanted electric signals that are not part of the Doppler audio signal and to filter out electronic noise signals that may be created by the probe 54. For example, electronic noise signals might be caused by the supply voltage $V_{DD}$ and the biasing voltage $V_B$, as well as by the electrical equipment in the room where the medical diagnostic device 50 is being used. Another function of the bandpass filter 101 is to smooth and convert the triangle wave voltage output signal from the frequency modulator 98 so that it becomes a sine wave voltage output signal from the bandpass filter 101. As discussed above, the SFG455B Ceramic Filter manufactured by muRata Erie of Smyrna, Ga., can be used in this invention for the bandpass filter 101. The electrical specifications and the operational characteristics for the SFG455B Ceramic Filter are given in muRata Erie Ceramic Filters, catalog no. P-03-B, page 12. The bandpass filter 101 is preferably centered at 455 KHz and preferably passes signals having frequencies between 440 KHz and 470 KHz. The bandpass filter 101 attenuates and filters electric signals having frequencies below 440 KHz and electric signals having frequencies above 470 KHz. Therefore, the output signal from the bandpass filter 101 on lead 308 is a frequency modulated sine wave voltage signal that has a center frequency of 455 KHz, whose frequency varies between 440 KHz and 470 KHz, and that has an amplitude that is between plus $V_{D1}$ volts and minus $V_{D1}$ volts.

Referring now to FIG. 15, the output signal from the bandpass filter 101 on lead 308 is the input signal to the voltage-to-current converter circuit 102, which creates two output currents on leads 308 and 310, respectively, that vary in intensity as a function of the voltage amplitude in the signal on the input lead 308. The voltage-to-current converter 102 converts the voltage of the frequency modulated sine wave voltage input signal from the bandpass filter 101 into a corresponding frequency modulated sine wave current output signal that is used to drive the infrared LEDs 104 $LED_1$, $LED_2$, $LED_3$, $LED_4$, $LED_5$, and $LED_6$. This conversion allows the LEDs 104 $LED_1$, $LED_2$, $LED_3$, $LED_4$, $LED_5$, and $LED_6$ to emit frequency modulated sine wave infrared light signals that correspond to the frequency modulated triangle wave voltage output signal from the frequency modulator 98. The capacitor $C_{10}$ acts as a block to prevent any DC voltage bias from the output of the bandpass filter 101 from existing on the input signal to the voltage-to-current converter 102.

The voltage-to-current converter 102 preferably, but not necessarily, includes two operational amplifiers $OA_1$ and $OA_2$, because separating the LEDs 104 into two groups, one group including LEDs 104 $LED_1$, $LED_2$, and $LED_3$ and the second group including $LED_4$, $LED_5$ and $LED_6$, allows use of lower supply voltages $V_1$ and $V_2$, and hence lower battery 107 voltage. The LF353 operational amplifiers manufactured by National Semiconductor, Inc., of Santa Clara, Calif., can be used in this invention in the voltage-to-current converter circuit 102. The configurations for both operational amplifiers $OA_1$ and $OA_2$ are identical and serve the same function. That is, the voltage $V_1$ serves the same function and has the same value as the voltage $V_2$, the resistor $R_{11}$ serves the same function and has the same value as the resistor $R_{15}$, the resistor $R_{12}$ serves the same function and has the same value as the resistor $R_{16}$, the resistor $R_{14}$ serves the same function and has the same value as the resistor $R_{17}$, the capacitor $C_8$ has the same value and serves the same function as the capacitor $C_9$, the transistor $Q_1$ is identical to and serves the same function as the transistor $Q_2$. The LED 104 $LED_1$ is identical to, and serves the same function as, the LED 104 $LED_4$—both are narrow beam positioned as to achieve maximum reflection off of the walls or the ceilings in the room where the medical diagnostic device 50 is being used, as will be described in more detail below. The LEDs 104 $LED_2$, $LED_3$, $LED_5$, and $LED_6$ are identical, serve the same function, and are wide beam positioned so as to maximize coverage in the room where the medical diagnostic device 50 is being used, as will also be described in more detail below. Since the configurations for the operational amplifiers $OA_1$ and $OA_2$ are identical and serve the same function, only the configuration for operational amplifier $OA_1$ will be discussed and described below.

Figure 13:
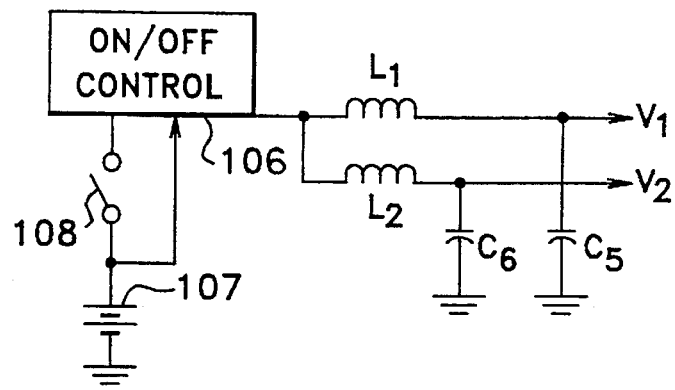
FIG. 13 shows a schematic diagram power supply portion of the electronic circuitry of the probe of FIG. 1 constructed to provide the voltage conversion functions of the voltage-to-current converter according to the present invention.

The operational amplifier $OA_1$, the resistor $R_{12}$, and the transistor $Q_1$ are arranged in a negative feedback configuration so as to function as a voltage-to-current converter with resistor $R_{11}$. This type of circuit configuration is well known to people having ordinary skill in the art. The voltages $V_1$ and $V_2$, in addition to the voltage $V_{DD}$ discussed above, are provided by the power supplies 109 in the probe 54. For example, as shown in FIG. 13, the voltages $V_1$ and $V_2$ can be created by coupling the rechargeable battery 107 to the capacitors $C_5$ and $C_6$ and the inductors $L_1$ and $L_2$ which act as an AC noise filter to provide the dean DC voltages $V_1$ and $V_2$. The voltage $V_1$ is equal to the voltage $V_2$, and can be, for example, 7.2 volts. The voltage is the required supply voltage to power the operational amplifier $OA_1$, and can be, for example, 12 volts. The capacitor $C_8$ provides an AC ground for the voltage $V_{DD}$ so that only DC voltage is supplied to the operational amplifier $OA_1$.

The voltage signal at the positive terminal 312 of the operational amplifier $OA_1$ includes a DC voltage signal and an AC voltage signal. The DC voltage signal at the positive terminal 312 of the operational amplifier $OA_1$ is created by the voltage $V_2$, the diode $D_1$, the capacitor $C_7$, and the resistors $R_9$ and $R_{10}$. The AC voltage signal at the positive terminal 312 of the operational amplifier $OA_1$ is provided from the frequency modulator 98, the bandpass filter 101, and the capacitor $C_{10}$, as previously discussed.

The voltage $V_{D1}$ is the voltage drop over the diode $D_1$ created by current flowing through the diode $D_1$. The capacitor $C_7$ provides an AC ground for any AC signals that may be created by the voltage $V_2$. The resistor $R_9$ is a load resistor for the current flowing out of the diode $D_1$. The resistor $R_{10}$ couples the DC bias voltage created by the voltage $V_2$, the capacitor $C_7$, and the resistor $R_9$ to the positive terminal 312 input of the operational amplifier $OA_1$. The resistor $R_{10}$ also provides a high resistance for AC signals created by the voltage $V_2$ from the positive terminal 312 input of the operational amplifier $OA_1$. Since the input resistance for the operational amplifier $OA_1$ is very high, there is no DC current flowing into the positive terminal 312 of the operational amplifier $OA_1$. There is also no DC current flowing through the capacitor $C_{10}$. Therefore, no current flows through the resistor $R_{10}$, and there is no voltage drop over the resistor $R_{10}$. Therefore, the DC voltage signal at the positive terminal 312 of the operational amplifier $OA_1$ is equal to $V_2$ minus $V_{D1}$ volts.

As previously discussed, the AC voltage signal at the positive terminal 312 of the operational amplifier $OA_1$ is the frequency modulated sine wave voltage signal created by the frequency modulator 98, the bandpass filter 101, and the capacitor $C_{10}$. The output signal from the capacitor $C_{10}$ is a frequency modulated sine wave voltage signal that has a center frequency of 455 KHz, whose frequency varies between 440 KHz and 470 KHz, and that has an amplitude that varies between plus $V_{D1}$ volts and minus $V_{D1}$ volts. Therefore, the total voltage signal at the positive terminal 312 of the operational amplifier $OA_1$, comprised of the DC voltage signal plus the AC voltage signal, has a range between $V_2$ volts and $V_2$ minus $2V_{D1}$ volts.

Due to the high gain of the operational amplifier $OA_1$ and the negative feedback configuration established with the operational amplifier $OA_1$ by the use of resistor $R_{12}$ and transistor $Q_1$, the voltage at the negative terminal 313 of the operational amplifier $OA_1$ is equal to the voltage at the positive terminal 312 of the operational amplifier $OA_1$. Therefore, the voltage at the negative terminal 313 of the operational amplifier $OA_1$ also varies between $V_2$ volts and $V_2$ minus $2V_{D1}$ volts.

Having a variable voltage level at the negative terminal 313 of the operational amplifier $OA_1$ also causes the current flowing through the resistor $R_{11}$ to vary. The current $I_{R11}$ flowing through the resistor $R_{11}$ will vary between the current levels provided by the following equations:

$$I_{R11} = \frac{V_2 - V_2}{R_{11}} = 0 \quad (1)$$

and Therefore, the AC current $I_{R11}$ flowing through the resistor $R_{11}$ ranges from zero (0) amperes to $2V_{D1}/R_{11}$ amperes. Consequently, the current $I_{R11}$ depends only on the voltage $V_{D1}$ and the $$I_{R11} = \frac{V_2 - (V_2 - 2V_{D1})}{R_{11}} = \frac{2V_{D1}}{R_{11}} \quad (2)$$

resistor $R_{11}$ and does not depend on the voltage $V_2$. As the voltage in the rechargeable battery 107 becomes depleted through use, the voltage $V_2$ will also become reduced. The voltage drop $V_{D1}$ across the diode $D_1$, however, will remain approximately constant. With the components shown in this embodiment, the voltage $V_{D1}$ across the diode $D_1$ will remain approximately 0.55 volts. Therefore, the reduction in charge in the rechargeable battery 107 and the reduction of the voltage $V_2$ will not affect either the voltage $V_{D1}$ or the current $I_{R11}$.

Since the negative terminal 313 of the operational amplifier $OA_1$ has a very high input impedance, none of the current $I_{R11}$ will flow into the negative terminal 313 of the operational amplifier $OA_1$. The current $I_{LED}$ flowing through the LEDs 104 $LED_1$, $LED_2$, and $LED_3$ is equal to $((\beta-1)/\beta) \times I_{R11}$ where $\beta$ is the AC gain of the transistor $Q_1$ and $\beta$ is typically equal to sixty (60) or greater. For the example components shown in this embodiment, the current $I_{LED}$ varies between zero (0) amperes and 0.092 amperes. The resistor $R_{14}$ is used to provide a means of sampling the current signal that flows through the infrared LEDs 104 $LED_1$, $LED_2$, and $LED_3$. The amount of infrared light emitted by the infrared LEDs 104 $LED_1$, $LED_2$, and $LED_3$ is linearly related to the amount of the current $I_{LED}$ that flows through the infrared LEDs 104 $LED_1$, $LED_2$, and $LED_3$. The infrared sine wave light signal emitted by the infrared LEDs 104 $LED_1$, $LED_2$, and $LED_3$ has a varying intensity, a constant peak to peak amplitude, a center frequency of 455 KHz, and is frequency modulated between 440 KHz and 470 KHz.

Referring now to FIG. 16, the frequency modulated infrared sine wave light signals emitted by the six infrared LEDs 104 $LED_1$, $LED_2$, $LED_3$, $LED_4$, $LED_5$, and $LED_6$ are detected in the photodetectors 120 $DET_1$, $DET_2$, $DET_3$, and $DET_4$ located on the base unit 52. As discussed above and as shown in FIGS. 7, 8, and 9, the photodetectors 120 $DET_1$, $DET_2$, $DET_3$, and $DET_4$ are arranged on the base unit 52 so that at least one of the infrared light signals emitted by the LEDs 104 $LED_1$, $LED_2$, $LED_3$, $LED_4$, $LED_5$, and $LED_6$ on the probe 54 are detected by the photodetectors 120 $DET_1$, $DET_2$, $DET_3$, and $DET_4$. The voltage $V_3$ is generated by the power supplies 156 located in the base unit 52 and can be, for example, 7.5 volts. The resistor $R_{18}$ and the capacitor $C_{11}$ act as a filter to reduce noise in the circuit. Likewise, the resistor $R_{19}$ and the capacitor $C_{12}$ act as a filter to reduce noise in the circuit.

The resistor $R_{20}$, the capacitor $C_{13}$ and the inductor $L_3$ act together to create the resonant circuit 122 which converts the current signal output of the photodetectors 120 $DET_1$, $DET_2$, $DET_3$, and $DET_4$ into a voltage signal which is the input signal to the preamplifier 124. Furthermore, the resonant circuit 122 limits the bandwidth of the input signals provided to the preamplifier 124.

The output signal of the resonant circuit 122 on lead 314 is the input signal to the preamplifier circuit 124, which includes the resistors $R_{21}$, $R_{22}$, $R_{23}$, and $R_{24}$, the capacitors $C_{14}$ and $C_{15}$, and the transistors $Q_3$ and $Q_4$. The preamplifier 124 is configured as a standard cascade amplifier—a type of amplifier that is well known to people having ordinary skill in the art. The cascade configured preamplifier 124 has high power gain, high input impedance, and low noise. The input to the preamplifier 124 is provided at lead 314 shown in FIG. 16, while the output from the preamplifier 124 is provided at lead 316. The resistors $R_{21}$ and $R_{22}$ provide the necessary voltage bias for the transistor $Q_3$. The resistor $R_{23}$ provides the necessary voltage bias for the transistor $Q_4$. The capacitor $C_{14}$ provides an AC ground for the gate of the transistor $Q_3$. The capacitor $C_{15}$ provides an AC bypass for the resistor $R_{23}$.

The output signal of the preamplifier 124 at lead 316 is a sine wave frequency modulated voltage signal and is the input signal on lead 316 to the bandpass filter 126. As discussed above, the SFG455B Ceramic Filter manufactured by muRata Erie of Smyrna, Ga., can be used in this invention for the bandpass filter 126. The bandpass filter 126 attenuates and filters electric signals from the preamplifier 124 that have frequencies below 440 KHz and electric signals that have frequencies above 470 KHz. The bandpass filter 126 is used to filter out unwanted signals that did not originate from the six infrared LEDs 104 $LED_1$, $LED_2$, $LED_3$, $LED_4$, $LED_5$, and $LED_6$ on the probe 54 that are detected by the photodetectors 120 $DET_1$, $DET_2$, $DET_3$, and $DET_4$ and to filter out electronic noise signals that may be created by the base unit 52 or by light and equipment located where the medical diagnostic device 50 of this invention is being used.

The output signal from the bandpass filter 126 on lead 318 is the input signal to frequency demodulator 128 shown in FIG. 17. As discussed above, the NE/SA604A High-Performance Low-Power FM IF System manufactured by Phillips (formerly the Signetics Company) can be used in this invention for the frequency demodulator 128. The electrical specifications and operational characteristics for the Signetics NE/SA604A High-Performance Low-Power FM IF System are provided in the Signetics Linear Data Manual, Volume 1: Communications, copyrighted 1988. The voltage $V_4$ is generated by the power supplies 156 located in the base unit 52 and can be, for example, 7.5 volts. The resistor $R_{13}$ and the capacitor $C_{27}$ act as a filter to reduce noise in the circuit.

The purpose of the frequency demodulator 128, as discussed above, is to convert the 440 KHz to 470 KHz frequency modulated sine wave signal to an audio signal having the same characteristics as the Doppler audio signal which is the input to the frequency modulator 98 in probe 54.

Figure 11:
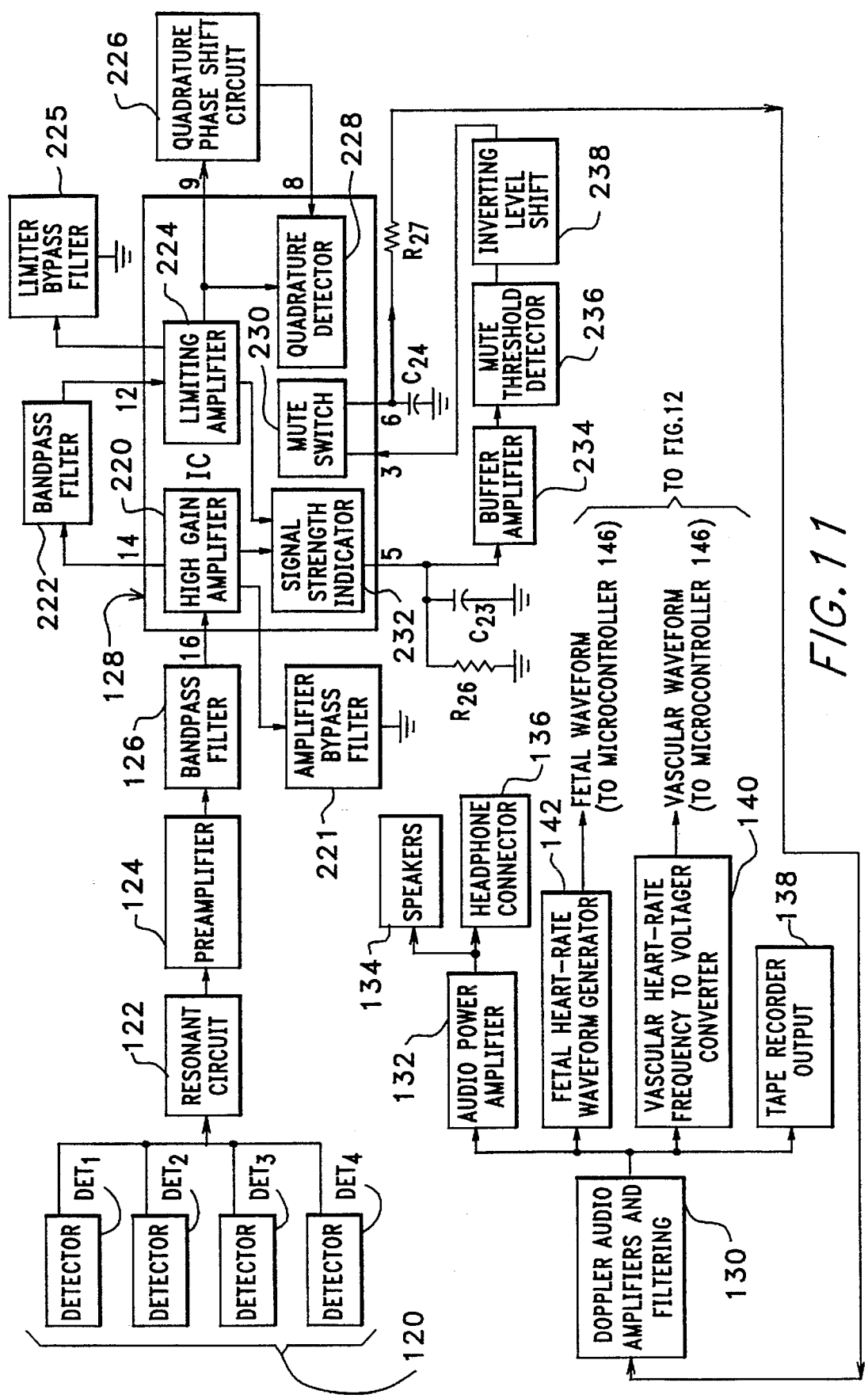
FIG. 11 shows a functional block diagram of the detection, amplification, demodulation, and waveform generation portion of the electronic circuitry of the base unit shown in FIG. 1.

The schematic diagram of the frequency demodulator 128 and its supporting electronic circuitry are shown in FIG. 17, and the operational block diagram for the frequency demodulator 128 is shown in FIG. 11. Therefore, the following description of the frequency demodulator 128 and its associated circuits requires references to both FIGS. 4 and 10 simultaneously. The input signal on pin 16 (see FIG. 17) to the frequency demodulator 128 is the output signal on lead 318 from bandpass filter 126 (see FIG. 16), as just described above. This input signed on lead 318 and on pin 16 (see FIG. 17) first passes through the internal high gain amplifier 220 (see FIG. 11) before exiting the frequency demodulator 128 on pin 14 (see FIG. 17). The capacitors $C_{16}$ and $C_{17}$ shown in FIG. 17 comprise the amplifier bypass filter 221 shown in FIG. 11 and provide the necessary coupling and filtering for the internal high gain amplifier 220.

The electric signal exiting the frequency demodulator 128 on pin 14 passes through the bandpass filter 222 (see FIGS. 4 and 10) before returning as an input to the frequency demodulator 128 on pin 12 (see FIG. 17). The SFG455B Ceramic Filter manufactured by muRata Erie of Smyrna, Ga., can be used in this invention for the bandpass filter 222. The bandpass filter 222 attenuates and filters electric signals that have frequencies below 440 KHz and electric signals that have frequencies above 470 KHz.

The output signal from the bandpass filter 222 is an input signal to the frequency demodulator 128 on pin 12 (see FIG. 17). The signal passes through the internal limiting amplifier 224 (see FIG. 11) which clips the input signal so that the output signal of the internal limiting amplifier 224 is a square wave signal. The capacitors $C_{18}$ and $C_{19}$ shown in FIG. 17 comprise the limiter bypass filter 225 shown in FIG. 11 and provide filtering that the internal limiting amplifier 224 needs for stability.

The square wave output signal from the internal limiting amplifier 224 is an output signal on pin 9 of the frequency demodulator 128 (see FIG. 17) which then passes through the phase shift circuit 226 (see FIG. 11) before re-entering the frequency demodulator 128 on pin 8 (see FIG. 17). The phase shift circuit 226, comprising capacitors $C_{20}$, $C_{21}$, and $C_{22}$, the resistor $R_{25}$, and the inductor $L_4$ in FIG. 17, shifts the phase of the square wave output signal from the internal limiting amplifier 224. The amount of the phase shift $\Phi$ of the square wave signal in the phase shift circuit 226 is approximated by:

where $$\Phi = \frac{\Pi}{2} - \arctan(Q_0 \gamma) \quad (3)$$

$$Q_0 = \omega_0 R_{24}(C_{21} + C_{22}) \quad (4)$$

and $$\gamma = \frac{\omega}{\omega_0} - \frac{\omega_0}{\omega} \quad (5)$$

where $$\omega_0 = 2\Pi(455 \times 10^3) \quad (6)$$

and $$\omega = 2\Pi(f_i) \quad (7)$$

where $f_i$ is equal to the instantaneous frequency of the input signal to the phase shift circuit 226. The phase shifted square wave output signal from the phase shift circuit 226 becomes an input signal on pin 8 (see FIG. 17) to the internal quadrature detector 228 (see FIG. 11). The square wave output signal from the internal limiting amplifier 224 is also passed directly to the internal quadrature detector 228, as illustrated in FIG. 11. For general information on quadrature detectors, see Herbert L. Krauss et at., SOLID STATE RADIO ENGINEERING, pages 310–314, published by John Wiley & Sons of New York City, (1980). The internal quadrature detector 228 multiplies the phase shifted square wave signal and the nonphase shifted square wave signal to create an electric signal that varies in amplitude at a frequency in the audio range. In other words, the output signal of the internal quadrature detector 228 has a frequency that is a function of the rate of change of the frequency of the nonphase shifted input signal and has an amplitude that is a function of the instantaneous deviation from 455 KHz of the frequency of the nonphase shifted input signal.

The output signal from the internal quadrature detector 228 is an input signal to the internal mute switch 230 (see FIG. 11). The internal mute switch 230 provides the signal from the internal quadrature detector 228 as an output signal on pin 6 of the frequency demodulator 128 (see FIG. 17) when the probe 54 is turned "on" and when the amplitude of the electric signal from the internal quadrature detector 228 exceeds a predetermined and preset threshold value. If the probe 54 is turned "off," or if the amplitude of the electric signal that the internal mute switch 230 receives from the internal quadrature detector 228 does not exceed the predetermined and preset threshold value, the internal mute switch 230 provides no output signal on pin 6 of the frequency demodulator 128.

Determination of whether the amplitude of the signal received by the internal mute switch 230 from the internal quadrature detector 228 exceeds the predetermined and preset threshold value is accomplished by the internal signal strength indicator 232, the buffer amplifier 234, the mute threshold detector 236, and the inverting level shifter 238, all of which are shown in FIG. 11. As shown in FIG. 11, the internal high gain amplifier 220 and the internal limiting amplifier 224 in the frequency demodulator 128 provide an output electric signal to the internal signal strength indicator 232. The output signal from the internal signal strength indicator 232 on pin 5 of the frequency demodulator 128 (see FIG. 17) is an input signal on lead 320 to the buffer amplifier 234 in FIG. 18. The output signal of the internal signal strength indicator 232 is proportional to the signal strength at the input pin 16 of the frequency demodulator 128 and is in the form of a DC current. The resistor $R_{26}$ in FIG. 17 converts the DC current output signal on pin 5 of frequency demodulator 128 from the signal strength indicator 232 (FIG. 11) to a voltage signal. The capacitor $C_{23}$ in FIG. 17 eliminates short current changes in the output signal from the internal signal strength indicator 232.

Figure 18:
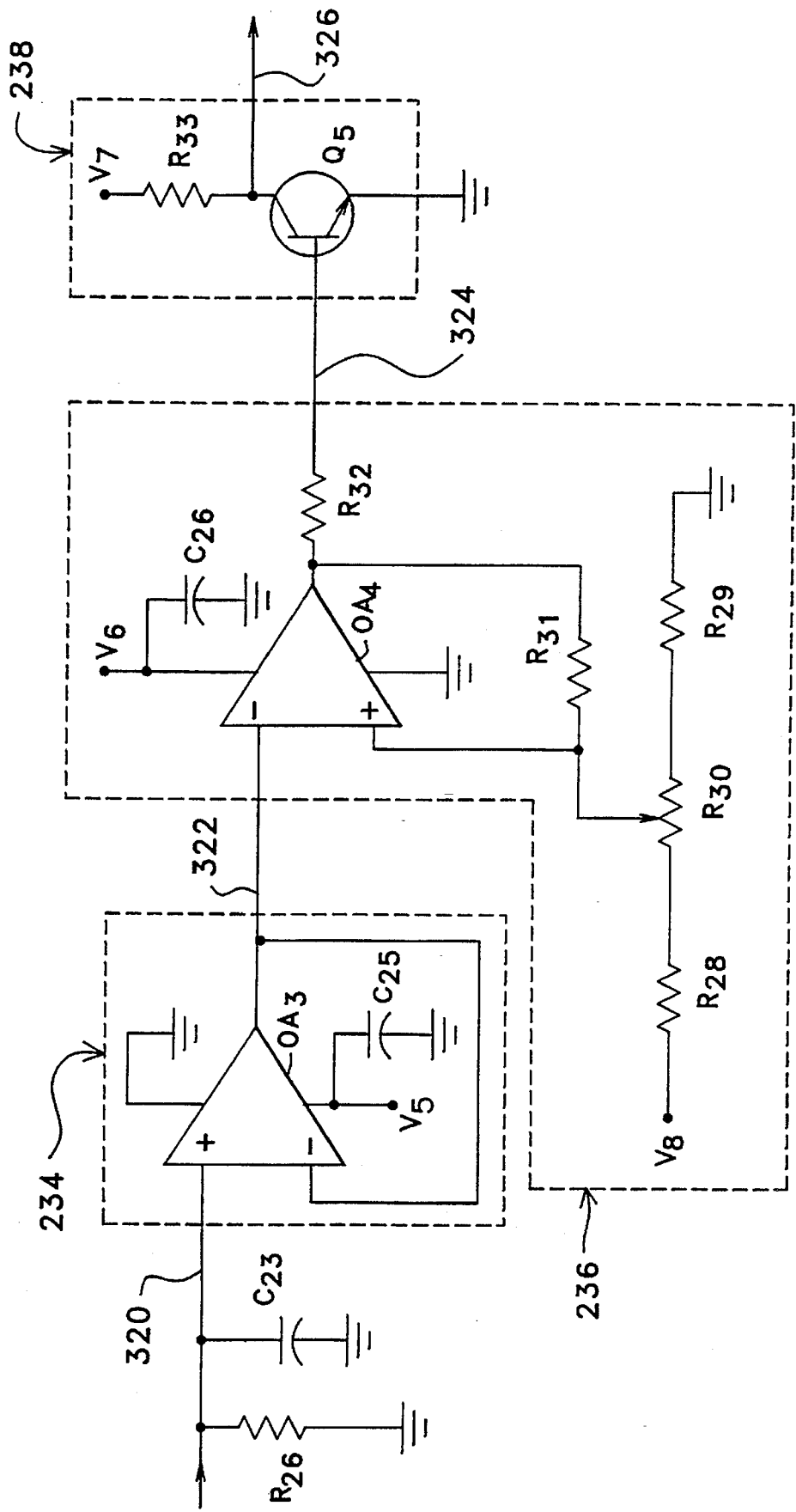
FIG. 18 shows a schematic diagram of the buffer amplifier, mute threshold detector, and inverting level shifter portion of the electronic circuitry of the base unit of FIG. 1 constructed to provide the signal mute functions of the base unit according to the present invention.

The buffer amplifier 234 in FIG. 18 lowers the impedance of the signal on lead 320 and provides an input signal on lead 322 to the mute threshold detector 236 in FIG. 18, which compares the signal strength of the input signal on lead 322 to the predetermined and preset threshold value discussed above. If the signal strength of the input signal to the mute threshold detector 236 is greater than the threshold value, the mute threshold detector 236 supplies a negative voltage signal to the inverting level shifter 238. The inverting level shifter 238 converts the negative voltage signal to a positive logic level signal needed to have the internal mute switch 230 provide an output signal on pin 6 of the frequency demodulator 128. If the signal strength of the input signal to the mute threshold detector 236 is not greater than the threshold value, the mute threshold detector 236 provides a positive voltage signal to the inverting level shifter 238. The inverting level shifter 238 converts the positive voltage signal to a negative logic level signal needed to have the internal mute switch 230 not provide an output signal on pin 6 of the frequency demodulator 128.

The output signal from the frequency demodulator 128 on pin 6 (see FIG. 17) is low pass filtered by the capacitor $C_{24}$. The resistor $R_{27}$ prevents signals from other circuits in the base unit 52 from reaching the frequency demodulator 128. The output signal from the low pass filter 240 on lead 324 is an input signal to the Doppler audio controller 130 shown in FIG. 11 and discussed above.

The schematic diagram for the buffer amplifier 234, mute threshold detector 236, and the inverting level shifter 238 are shown in FIG. 18. The voltages $V_5$, $V_6$, and $V_7$ are supplied by the power supplies 156 (see FIG. 12) in the base unit 52 and all three can be, for example, 7.5 volts. The capacitor $C_{25}$ acts as an AC ground for the voltage $V_5$. Likewise, the capacitor $C_{26}$ acts as an AC ground for the voltage $V_6$.

The input of lead 320 to the buffer amplifier 234 is on the positive terminal of the operational amplifier $OA_3$. The buffer amplifier 234 includes the capacitor $C_{25}$ and the operational amplifier $OA_3$ in a standard and well-known buffer amplifier configuration to buffer the frequency demodulator 128 from the mute threshold detector 236. The LT1013 operational amplifier manufactured by Linear Technology of Milpitas, Calif., can be used in the buffer amplifier 234.

The output signal from the buffer amplifier 234 on lead 322 is the input signal to the mute threshold detector 236, as shown in FIG. 18. The mute threshold detector 236 includes the capacitor $C_{26}$ and the resistors $R_{28}$, $R_{29}$, $R_{30}$, $R_{31}$, and $R_{32}$. The input signal to the mute threshold detector 236 is on the negative terminal of the operational amplifier $OA_4$. The LT1013 operational amplifier manufactured by Linear Technology of Milpitas, Calif., can be used in this invention in the mute threshold detector 236. The fixed voltage $V_8$, the fixed value resistors $R_{28}$ and $R_{29}$, and the variable resistor $R_{30}$ set the signal threshold to be used in the mute threshold detector 236. The resistor $R_{31}$ is used to create a positive feedback signal, which prevents the output of the operational amplifier $OA_4$ from changing states if the change in the input signal level is very small. The resistor $R_{32}$ is used to set the input current level to transistor $Q_5$. The voltage $V_8$ is supplied by the power supplies 156 in the base unit 52 and can be, for example 7.5 volts.

As discussed above, if the signal strength of the output signal from the buffer amplifier 234 is greater than the threshold value set by the voltage $V_8$ and the resistors $R_{28}$, $R_{29}$, and $R_{30}$, the mute threshold detector 236 supplies a negative voltage output signal on lead 324 to the inverting level shifter 238. If the signal strength of the output signal from the buffer amplifier 234 is not greater than the threshold value set by the voltage $V_8$ and the resistors $R_{28}$, $R_{29}$, and $R_{30}$, the mute threshold detector 236 provides a positive voltage output signal on lead 324 to the inverting level shifter 238.

The inverting level shifter 238 shown in FIG. 18 includes the resistor $R_{33}$ and the transistor $Q_5$. The output lead 326 of the inverting level shifter 238 in FIG. 18 is connected to pin 3 of the frequency demodulator 128 in FIGS. 4 and 10. The inverting level shifter 238 converts a negative voltage signal provided by the mute threshold detector 236 to the logic level signal needed on pin 3 of frequency demodulator 128 to have the internal mute switch 230 in the frequency demodulator 128 provide an output signal on pin 6 of the frequency demodulator 128. Similarly, the inverting level shifter 238 converts a positive voltage signal provided by the mute threshold detector 236 to the logic level signal needed to have the internal mute switch 230 in the frequency demodulator 128 not provide an output signal on pin 6 of the frequency demodulator 128. A positive signal provided by the mute threshold detector 236 at lead 324 in FIG. 18 activates the transistor $Q_5$ so that current flows through the resistor $R_{33}$ which causes the voltage at lead 326 to be nearly equal to zero (0). A negative signal provided by the mute threshold detector 236 at lead 324 does not activate the transistor $Q_5$. Therefore, no current flows through the resistor $R_{33}$, and the voltage at lead 326 is equal to $V_7$. Inverter circuits such as the inverting level shifter 238 are well known to people having ordinary skill in the art.

For purposes of examples and not for limitations, the exemplary component values for the resistors, capacitors, and inductors listed in the following table can be used in the circuits of the diagnostic device 50, although other component designs can also be used.

| Component | Identifier | Value | Manufacturer | Part Number |
|---|---|---|---|---|
| Resistor | $R_1$ | 1,800 ohms | | |
| Resistor (variable) | $R_2$ | 0–10,000 ohms | | |
| Resistor (variable) | $R_3$ | 0–5,000 ohms | | |
| Resistor | $R_4$ | 6,800 ohms | | |
| Resistor | $R_5$ | 68,000 ohms | | |
| Resistor | $R_6$ | 3,300 ohms | | |
| Resistor (variable) | $R_7$ | 0–5,000 ohms | | |
| Resistor | $R_8$ | 2,200 ohms | | |
| Resistor | $R_9$ | 10,000 ohms | | |
| Resistor | $R_{10}$ | 12,000 ohms | | |
| Resistor | $R_{11}$ | 12 ohms | | |
| Resistor | $R_{12}$ | 100 ohms | | |
| Resistor | $R_{13}$ | 10 ohms | | |
| Resistor | $R_{14}$ | 1 ohm | | |
| Resistor | $R_{15}$ | 12 ohms | | |
| Resistor | $R_{16}$ | 100 ohms | | |
| Resistor | $R_{17}$ | 1 ohm | | |
| Resistor | $R_{18}$ | 1,000 ohms | | |
| Resistor | $R_{19}$ | 100 ohms | | |
| Resistor | $R_{20}$ | 10,000 ohms | | |
| Resistor | $R_{21}$ | 10,000 ohms | | |
| Resistor | $R_{22}$ | 15,000 ohms | | |
| Resistor | $R_{23}$ | 1,000 ohms | | |
| Resistor | $R_{24}$ | 1,500 ohms | | |
| Resistor | $R_{25}$ | 20,000 ohms | | |
| Resistor | $R_{26}$ | 100,000 ohms | | |
| Resistor | $R_{27}$ | 100 ohms | | |
| Resistor | $R_{28}$ | 20,000 ohms | | |
| Resistor | $R_{29}$ | 5,600 ohms | | |
| Resistor (variable) | $R_{30}$ | 0–5,000 ohms | | |
| Resistor | $R_{31}$ | 220,000 ohms | | |
| Resistor | $R_{32}$ | 47,000 ohms | | |
| Resistor | $R_{33}$ | 47,000 ohms | | |
| Capacitor | $C_1$ | 0.04 microfarads | | |
| Capacitor | $C_2$ | 0.047 microfarads | | |
| Capacitor | $C_3$ | 220 picofarads | | |
| Capacitor | $C_4$ | 4.7 microfarads | | |
| Capacitor | $C_5$ | 47 microfarads | | |
| Capacitor | $C_6$ | 47 microfarads | | |
| Capacitor | $C_7$ | 0.1 microfarads | | |
| Capacitor | $C_8$ | 0.047 microfarads | | |
| Capacitor | $C_9$ | 0.047 microfarads | | |
| Capacitor | $C_{10}$ | 0.001 microfarads | | |
| Capacitor | $C_{11}$ | 0.1 microfarads | | |
| Capacitor | $C_{12}$ | 0.1 microfarads | | |
| Capacitor | $C_{13}$ | 120 picofarads | | |
| Capacitor | $C_{14}$ | 0.1 microfarads | | |
| Capacitor | $C_{15}$ | 0.1 microfarads | | |
| Capacitor | $C_{16}$ | 0.1 microfarads | | |
| Capacitor | $C_{17}$ | 0.1 microfarads | | |
| Capacitor | $C_{18}$ | 0.1 microfarads | | |
| Capacitor | $C_{19}$ | 0.1 microfarads | | |
| Capacitor | $C_{20}$ | 0.1 microfarads | | |
| Capacitor | $C_{21}$ | 180 picofarads | | |
| Capacitor | $C_{22}$ | 10 picofarads | | |
| Capacitor | $C_{23}$ | 0.1 microfarads | | |
| Capacitor | $C_{24}$ | 0.0033 microfarads | | |
| Capacitor | $C_{25}$ | 0.1 microfarads | | |
| Capacitor | $C_{26}$ | 0.1 microfarads | | |
| Capacitor | $C_{27}$ | 10 microfarads | | |
| Inductor | $L_1$ | 47 microhenries | | |
| Inductor | $L_2$ | 47 microhenries | | |
| Inductor | $L_3$ | 680 microhenries | | |
| Inductor | $L_4$ | 680 microhenries | | |
| Transistor | $Q_1$ | | Motorola | 2N3906 |
| Transistor | $Q_2$ | | Motorola | 2N3906 |
| Transistor | $Q_3$ | | Siliconix | SST309 |
| Transistor | $Q_4$ | | Siliconix | SST309 |
| Transistor | $Q_5$ | | Motorola | 2N3904 |

-continued

| Component | Identifier | Value | Manufacturer | Part Number |
|---|---|---|---|---|
| Operational Amplifier | OA$_1$ | | National Semiconductor | LF353 |
| Operational Amplifier | OA$_2$ | | National Semiconductor | LF353 |
| Operational Amplifier | OA$_3$ | | Linear Technology | LT1013 |
| Operational Amplifier | OA$_4$ | | Linear Technology | LT1013 |

The remaining circuits for components, including the Doppler audio amplifiers and filtering 130, audio power amplifier 132, speakers 134, headphone connectors 136, tape recorder output 138, vascular heart rate frequency to voltage converter 140, and fetal heart-rate waveform generator 142, are all old and well-known in the art and do not form any part of this invention. Therefore, the circuits for these components need not be described further for purposes of explaining and understanding this invention.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

The embodiments of the invention in which an exclusive property or privilege is claimed are defined as follows:

1. Diagnostic apparatus for measuring physical phenomena occurring inside a body, comprising:
   a transmitter capable of generating acoustic waves and propagating said acoustic waves into said body, wherein said acoustic waves are capable of being altered in response to the physical phenomena occurring in said body such that said altered acoustic waves are indicative of the physical phenomena occurring in said body, and wherein said transmitter is located external of said body;
   a transducer capable of detecting said altered acoustic waves, said transducer being located external of said body and capable of generating an electric receiver signal having characteristics indicative of the physical phenomena;
   signal converter means connected to said transducer for converting said electric receiver signal to a frequency modulated sine wave current that is indicative of the physical phenomena;
   a plurality of light emitters connected to said signal converter means, which light emitters emit light with intensity that is a linear function of amplitude of the frequency modulated sine wave current;
   a light detector separated spatially from said light emitter and external of said body, which light detector is capable of producing an electric detector signal;
   signal processing means connected to said light detector for extracting information about said physical phenomena from said electric detector signal; and
   display means connected to said signal processing means for producing a display of said information.

2. The diagnostic apparatus of claim 1, wherein said display means is a visual display device.

3. The diagnostic apparatus of claim 1, wherein said display means is an audio speaker.

4. The diagnostic apparatus of claim 1, wherein said display means is a data storage device.

5. The diagnostic apparatus of claim 1, wherein each of said plurality of light emitters is directional in light emission and is oriented to emit light in a direction different from another one of said light emitters such that said plurality of light emitters emit light in a plurality of directions.

6. The diagnostic apparatus of claim 5, wherein said plurality of directions includes a first direction and a second direction that is opposite and parallel to said first direction.

7. The diagnostic apparatus of claim 6, wherein said plurality of directions includes a third direction that is orthogonal to both said first direction and said second direction.

8. The diagnostic apparatus of claim 5, wherein said plurality of directions includes a first direction and a second direction that is orthogonal to said first direction.

9. The diagnostic apparatus of claim 1, wherein said frequency modulated sine wave current has a frequency that varies between 440 kilohertz and 470 kilohertz.

10. The diagnostic apparatus of claim 9, wherein said frequency modulated sine wave current has a carrier signal frequency of 455 kilohertz.

11. Doppler ultrasound diagnostic apparatus for measuring physical phenomena occurring inside a body; comprising:
   a probe containing: (a) ultrasound transceiver means located external of said body for generating ultrasound acoustic waves and propagating said ultrasound acoustic waves within said body, for receiving echoes of said ultrasound acoustic waves, and for producing an electric receiver signal that is modulated as a function of Doppler frequency shift of the echoes; (b) a plurality of infrared light emitters positioned to emit light in a plurality of directions; and (c) driver circuit means connected to said ultrasound transceiver means and to said infrared light emitters for powering said infrared light emitters to produce harmonic free infrared light signals that are a function of said Doppler frequency shift of the echoes; and
   a base unit positioned remote from said probe, said base unit containing: (a) plurality of photodetector means oriented in a plurality of directions and responsive to said infrared light signals for producing an electric detector signal that is a function of said infrared light signals and of said Doppler frequency shift of the echoes; (b) signal processing means for deriving information from said electric detector signal that is indicative of said Doppler frequency shift and for producing display signals from said information for driving display equipment; and (c) display equipment connected to said signal processing means and responsive to said display signals to produce visual, audio, or storage displays of said information.

12. The diagnostic apparatus of claim 11, wherein said harmonic free infrared light signal has a frequency between 440 kilohertz and 470 kilohertz.

13. The diagnostic apparatus of claim 11, wherein said plurality of infrared light emitters on said probe include a first infrared light emitter that emits infrared light and a second infrared light emitter that emits infrared light in a direction that is opposite and parallel to said light emitted by said first infrared light emitter.

14. The diagnostic apparatus of claim 11, wherein said plurality of infrared light emitters on said probe include a first infrared light emitter that emits infrared light and a second infrared light emitter that emits infrared light in a direction that is orthogonal to said light emitted by said first infrared light emitter.

15. The diagnostic apparatus of claim 14, wherein said plurality of infrared light emitters on said probe include a third infrared light emitter that emits infrared light in a direction orthogonal to said infrared light emitted by said first infrared light emitter.

* * * * *